United States Patent
Huang et al.

(10) Patent No.: US 12,137,914 B2
(45) Date of Patent: Nov. 12, 2024

(54) ANASTOMOSIS SET, ANASTOMOTIC AUXILIARY AND THE METHOD THEREOF

(71) Applicant: VasoCollar, Inc., Tainan (TW)

(72) Inventors: Hsin-Lei Huang, Taipei (TW); Wei-Chen Hong, Taipei (TW); Cheng Tung Huang, Pleasanton, CA (US); Hang-Yi Lin, Taipei (TW); Hsin-Hui Huang, Taipei (TW)

(73) Assignee: Vasocollar, Inc (TW)

( * ) Notice: Subject to any disclaimer, the term of this patent is extended or adjusted under 35 U.S.C. 154(b) by 1045 days.

(21) Appl. No.: 16/679,541

(22) Filed: Nov. 11, 2019

(65) Prior Publication Data

US 2020/0187944 A1    Jun. 18, 2020

Related U.S. Application Data

(60) Provisional application No. 62/797,950, filed on Jan. 29, 2019, provisional application No. 62/760,050, filed on Nov. 13, 2018.

(51) Int. Cl.
| | |
|---|---|
| *A61B 17/11* | (2006.01) |
| *A61B 17/00* | (2006.01) |
| *A61B 17/06* | (2006.01) |

(52) U.S. Cl.
CPC ........ *A61B 17/11* (2013.01); *A61B 17/06166* (2013.01); *A61B 2017/00004* (2013.01);
(Continued)

(58) Field of Classification Search
CPC ............ A61B 17/11; A61B 2017/1107; A61B 2017/1132; A61B 2017/1135; A61B 2017/00991; A61B 17/0643; A61B 2017/1125; A61B 17/30; A61B 2017/1121; A61B 17/1128; A61B 17/0057; A61B 17/1204; A61B 2017/00601; A61B 2017/00654; A61B 2017/22067;
(Continued)

(56) References Cited

U.S. PATENT DOCUMENTS

| | | | |
|---|---|---|---|
| 4,635,636 A * | 1/1987 | Goldstein | A61B 17/11 269/45 |
| 8,926,655 B2 * | 1/2015 | Vidlund | A61B 17/0057 606/213 |

(Continued)

*Primary Examiner* — Brooke Labranche
*Assistant Examiner* — Lauren Dubose
(74) *Attorney, Agent, or Firm* — Jonathan D Feuchtwang

(57) ABSTRACT

An anastomosis set for anastomosing a first end to be anastomosed with a second end to be anastomosed, such anastomosis set comprising: a first manipulator, with a first telescoping part at a distal end thereof, the first telescoping part is used for telescoping toward the first end to be anastomosed; a second manipulator, with a second telescoping part at a distal end thereof, the second telescoping part is used for telescoping toward the second end to be anastomosed; and an anastomosis mechanism for anastomosing the first end to be anastomosed with the second end to be anastomosed; the first manipulator including a first exit part through which the first manipulator will be removed from the first end to be anastomosed after anastomosing; the second manipulator has a second exit part, through which the second manipulator will be removed from the second end to be anastomosed after anastomosing.

7 Claims, 40 Drawing Sheets

(52) U.S. Cl.
CPC ............... *A61B 2017/00991* (2013.01); *A61B 2017/1107* (2013.01)

(58) Field of Classification Search
CPC ............ A61B 2017/1103; A61B 17/10; A61B 2017/00557; A61B 2017/00858; A61F 2/064
USPC ......................................... 606/150, 152–156
See application file for complete search history.

(56) References Cited

U.S. PATENT DOCUMENTS

| | | | | |
|---|---|---|---|---|
| 2009/0254101 | A1* | 10/2009 | Morsi | A61B 17/11 606/139 |
| 2014/0052160 | A1* | 2/2014 | Singh | A61B 17/11 606/153 |
| 2016/0310117 | A1* | 10/2016 | Chin | A61B 17/12045 |

* cited by examiner

ANASTOMOSIS SET, ANASTOMOTIC AUXILIARY AND THE METHOD THEREOF

FIELD

An anastomosis set anastomosing, including: a first manipulator, a first telescoping part; a second manipulator, a second telescoping part used for telescoping; and an anastomosis mechanism, when the first and second telescoping parts are extended toward the first and second ends of the blood vessel to be anastomosed and mutually aligned to each other, the anastomosis mechanism will anastomose the first end of the blood vessel with the second end of the blood vessel to be anastomosed; the first manipulator has the first exit part from which it will be removed from the first end to be anastomosed; and the second manipulator has the second exit part from which it will be removed from the second end to be anastomosed.

The invention relates generally to an anastomosis set, and more particularly to an anastomosis set used for anastomosing a vascular junction.

BACKGROUND

There exists a need to join (anastomose) blood vessels supplying various organs or tissues. For example, during a post-mastectomy reconstruction, there frequently is a need to anastomose (join) an artery and a vein. Since it takes a relatively long amount of time to suture a blood vessel, the suturing of numerous blood vessels, can take a significant amount of time. Accordingly, there is a need for an improved anastomosis set which can reduce the amount of time needed to join blood vessels.

SUMMARY OF INVENTION

Disclosed is a first example anastomosis set for anastomosing a first end to be anastomosed with a second end to be anastomosed, such anastomosis set comprising: a first manipulator, with a first telescoping part at a distal end thereof, the first telescoping part is used for telescoping toward the first end to be anastomosed; a second manipulator, with a second telescoping part at a distal end thereof, the second telescoping part is used for telescoping toward the second end to be anastomosed; and an anastomosis mechanism for anastomosing the first end to be anastomosed with the second end to be anastomosed; the first manipulator including a first exit part through which the first manipulator will be removed from the first end to be anastomosed after anastomosing; the second manipulator has a second exit part, through which the second manipulator will be removed from the second end to be anastomosed after anastomosing.

The first example anastomosis set, further comprising an anastomotic aid device, at least one of the first manipulator and second manipulator are attached to the anastomotic aid device.

The anastomosis set of the first example, wherein the at least one of the first manipulator and second manipulator are moveably attached to anastomotic aid device.

The anastomosis set of the first example, wherein: the first telescoping part includes a first telescoping half and a second telescoping half that can be separated from each other, the first telescoping half and the second telescoping half cooperatively defining a first exit part; the second telescoping part includes a third telescoping half and a fourth telescoping half that can be separated from each other, the third telescoping half and the fourth telescoping half cooperatively defining a second exit part.

The anastomosis set of the first example, wherein the anastomosis mechanism is a suture mechanism.

The anastomosis set of the first example, wherein the anastomosis mechanism includes a first anastomotic device and a second anastomotic device, the first anastomotic device is equipped with plural piercing pins, the piercing pins being configured to pierce go through a wall of a blood vessel to be anastomosed.

The anastomosis set of the first example, wherein the anastomosis mechanism is a bendable clamping mechanism, and a first anastomosis end of such anastomosis mechanism is equipped with plural piercing pins.

The anastomosis set of the first example, further comprising a folding device having a first folding part and a second folding part that can be closed and opened mutually, wherein the first and second folding parts, respectively, are configured to fold a first and a second end of a blood vessel to be anastomosed.

According to a second example, the anastomosis set of the first example further comprises: an anastomotic auxiliary with a first embedding end and a second embedding end; wherein the first embedding end is configured to embed into a first end of a blood vessel to be anastomosed, and the second embedding end is configured to embed into a second end of the blood vessel to be anastomosed.

The anastomosis set of the second example, wherein the first manipulator is a clamp and the second manipulator is a clamp, the first manipulator having a first containing part and the second manipulator having a second containing part, whereby when the first embedding end is embedded into the first end of the blood vessel to be anastomosed and the second embedding end is embedded into the second end of the blood vessel to be anastomosed, and the first manipulator clamps onto such first end of the blood vessel to be anastomosed and the second manipulator clamps onto the second end of the blood vessel to be anastomosed, at least a part of the first embedding end is contained in the first containing part, and at least a part of such second embedding end is contained in the second containing part.

The anastomosis set of the second example, wherein the anastomotic auxiliary is formed by winding an elongate flake, the width of the long flake increases gradually from top to bottom, and such anastomotic auxiliary is formed by winding the elongate flake from bottom to top; wherein the anastomotic auxiliary can be unwound and restored into the elongate flake.

The anastomosis set of the second example, wherein the anastomotic auxiliary is formed by stacking a line repeatedly or by winding spirally; wherein the stacking or winding of such anastomotic auxiliary can be relieved and restored into a line.

The anastomosis set of the second example, wherein the anastomotic auxiliary is an elastomer and contains a fluid inside; wherein the anastomotic auxiliary has a re-closable opening through which the fluid may be added or released.

The anastomosis set the second example, wherein the anastomotic auxiliary includes plural lines and a removable auxiliary control unit; wherein the tortuosity of such plural lines can be adjusted by controlling an interval of the auxiliary control unit.

The anastomosis set of the second example, wherein the anastomotic auxiliary is bioabsorbable.

The anastomosis set of the preceding paragraph, wherein the anastomosis mechanism includes a C-shaped device which anastomoses the first end of the blood vessel to be anastomosed with the second end of the blood vessel to be anastomosed when the anastomotic auxiliary is bioabsorbing.

The anastomosis set of the second example, wherein the anastomotic auxiliary has a recycle unit, and a tear line is formed by extending spirally on such anastomotic auxiliary; wherein when pulling such recycle unit, the anastomotic auxiliary is gradually torn into a linear body along such tear line.

The anastomosis set of the second example, wherein a metal line is wound onto such anastomotic auxiliary to support it.

The anastomosis set of the second example, wherein the anastomotic auxiliary includes a first fusiform half and a second fusiform half, such first fusiform half has a first joint surface mutually joined with a second joint surface of the second fusiform half, the first and second fusiform halves having complimentary surfaces which engage with one another to prevent the first fusiform half from slipping relative to the second fusiform half.

The anastomosis set of the second example, wherein the anastomotic auxiliary has a hollow tube for body fluids to flow in it.

The anastomosis set of the second example, further comprising a makeup mechanism, which will make up an un-anastomosed gap at such first and second end to be anastomosed after removing such anastomotic auxiliary from the first and second ends of the blood vessel to be anastomosed.

The anastomosis set of the second example, wherein the anastomotic auxiliary has an exit part, and such anastomotic auxiliary is removed from such first and second ends of the blood vessel to be anastomosed through such exit part.

The anastomosis set of the second example, further comprising an anastomotic auxiliary removal aid, such anastomotic auxiliary removal aid removes the anastomotic auxiliary from such first and second end of the blood vessel to be anastomosed; wherein the anastomotic auxiliary removal aid includes a hollow tube and a removal device; wherein the hollow tube has an access in which such removal device locates; and such removal device is attached to the anastomotic auxiliary.

The anastomosis set of the second example, further comprising an anastomotic auxiliary removal aid, such anastomotic auxiliary removal aid removes the anastomotic auxiliary from such first and second end of the blood vessel to be anastomosed; wherein the anastomotic auxiliary removal aid includes an arcuate sheet component and a removal device; wherein the arcuate sheet component has a removal hole through which such removal device connects such anastomotic auxiliary.

The anastomosis set of the second example, wherein when the first embedding end is embedded into such first end of the blood vessel to be anastomosed, and such second embedding end is embedded into such second end of the blood vessel to be anastomosed, such anastomotic auxiliary will turn into any one of fusiform, tubular, rectangular, oval, flying saucer or cylindrical shape.

Disclosed is a third example anastomosis set used for anastomosing an end of a blood vessel to be anastomosed with a side to be anastomosed, such anastomosis set includes: a manipulator, with a telescoping part at a distal end, and such telescoping part is used for telescoping at such distal end; an anastomotic auxiliary having a first embedding end, a second embedding end, and a convex part in the middle of such first and second embedding end, such anastomotic auxiliary embeds the first and second embedding end into such side to be anastomosed to make the part of such side to be anastomosed outward to such convex part; and an anastomosis mechanism, which will anastomose such end to be anastomosed with such side to be anastomosed when the end to be anastomosed is telescoped by such telescoping part and such end and side to be anastomosed are mutually aligned to each other; wherein the manipulator has an exit part from which it will be removed from such end to be anastomosed after the end to be anastomosed has been anastomosed with the side to be anastomosed.

The anastomosis set of the third example, wherein the telescoping part includes a first telescoping half and a second telescoping half that can be separated from each other, thus forming the first exit part.

The anastomosis set of the third example, wherein the anastomosis mechanism is a suture mechanism, suturing such side to be anastomosed with the end of the blood vessel to be anastomosed.

The anastomosis set of the third example, it further includes a folding device, which is equipped with a first folding part and a second folding part that can be closed and opened mutually, wherein the end to be anastomosed folds a tube wall of such first and second folding part respectively by closing and opening them, and telescopes them outside such telescoping part.

The anastomosis set of the third example, wherein the anastomotic auxiliary is formed by winding a long flake, a width of such long flake increases gradually from top to bottom, and such anastomotic auxiliary is formed by winding the long flake from bottom to top; wherein the anastomotic auxiliary can be unwound and restored into the long flake.

The anastomosis set of the third example, wherein the anastomotic auxiliary is formed by stacking a line repeatedly or by winding spirally; wherein the stacking or winding of such anastomotic auxiliary can be relieved and restored into a line.

The anastomosis set of the third example, wherein the anastomotic auxiliary is an elastomer and contains liquid and/or gas inside; wherein the anastomotic auxiliary has an opening-closing hole, and such anastomotic auxiliary supplements or releases liquid and/or gas through such opening-closing hole.

The anastomosis set of the third example, wherein the anastomotic auxiliary includes plural lines and a removable auxiliary control unit; wherein the tortuosity of such plural lines can be adjusted by controlling an interval of such auxiliary control unit.

The anastomosis set of the third example, wherein the anastomotic auxiliary is a solid object which bioabsorbs in a human body.

The anastomosis set of the preceding paragraph, wherein the anastomosis mechanism includes a C-shaped device which anastomoses the end of the blood vessel to be anastomosed with the side of the blood vessel to be anastomosed when such solid object is dissolving.

The anastomosis set of the third example, wherein the anastomotic auxiliary has a recycle unit, and a tear line is formed by extending spirally on such anastomotic auxiliary; wherein when pulling such recycle unit, such anastomotic auxiliary is gradually torn into a linear body along such tear line.

The anastomosis set of the third example, wherein a metal line is wound onto such anastomotic auxiliary to support it.

The anastomosis set of the third example, wherein the anastomotic auxiliary includes a first fusiform half and a second fusiform half, such first fusiform half has a first joint surface mutually joined with a second joint surface of the second fusiform half, the first and second fusiform halves having complimentary shaped portions which engage to prevent such first and second fusiform half from mutual slipping.

The anastomosis set of the third example, wherein the anastomotic auxiliary has a hollow tube for body fluids to flow in it.

The anastomosis set of the third example, further comprising a makeup mechanism, which will make up an un-anastomosed gap between such end of the blood vessel to be anastomosed and such side to be anastomosed after removing such anastomotic auxiliary from the side of the blood vessel to be anastomosed.

The anastomosis set of the third example, wherein the anastomotic auxiliary has an exit part, and such anastomotic auxiliary is removed from such side to be anastomosed through such exit part.

The anastomosis set of the third example, further comprising an anastomotic auxiliary removal aid, wherein the anastomotic auxiliary removal aid is configured to remove the anastomotic auxiliary from such side of the vessel to be anastomosed; wherein the anastomotic auxiliary removal aid includes a hollow tube and a removal device; wherein the hollow tube has an access in which such removal device locates; and such removal device connects such anastomotic auxiliary.

The anastomosis set of the third example, further comprising an anastomotic auxiliary removal aid, such anastomotic auxiliary removal aid removes the anastomotic auxiliary from such side to be anastomosed; wherein the anastomotic auxiliary removal aid includes an arcuate sheet component and a removal device; wherein the arcuate sheet component has a removal hole, through which the removal device connects to the anastomotic auxiliary.

The anastomosis set of the third example, wherein when the anastomotic auxiliary is embedded into the side of the blood vessel to be anastomosed, the anastomotic auxiliary will turn into any one of fusiform, tubular, rectangular, oval, flying saucer or cylindrical shape.

Disclosed is a fourth example anastomosis set, comprising: an anastomotic auxiliary, at least a part of it is embedded into a body part to be anastomosed; and an anastomotic device, which anastomoses the body part to be anastomosed after the anastomotic auxiliary is embedded into the body part to be anastomosed; wherein the anastomotic auxiliary is embedded into the body part to be anastomosed in a first structural form and removed from such body part to be anastomosed in a second structural form, and the first structural form is different from the second structural form.

The anastomosis set of the fourth example, wherein the anastomotic auxiliary is formed by winding a long flake and in a winding structural form, the width of such long flake increases gradually from top to bottom, and such anastomotic auxiliary is formed by winding the long flake from bottom to top; wherein the anastomotic auxiliary can be unwound and restored into the long flake and in a unwound structural form.

The anastomosis set of the fourth example, wherein the anastomotic auxiliary is formed by stacking a line repeatedly or by winding spirally and in a columnar structural form or tubular structural form; wherein the stacking or winding of such anastomotic auxiliary can be relieved and restored into a line and in a linear structural form.

The anastomosis set of the fourth example, wherein the anastomotic auxiliary is an elastomer and contains a liquid and/or gas inside; wherein the anastomotic auxiliary has an opening-closing hole, and such anastomotic auxiliary supplements or releases liquid and/or gas through such opening-closing hole and in a shrunk structural form.

The anastomosis set of the fourth example, wherein the anastomotic auxiliary includes plural lines and a removable auxiliary control unit; wherein the tortuosity of such plural lines can be adjusted by controlling an interval of such auxiliary control unit.

The anastomosis set of the fourth example, wherein the anastomotic auxiliary includes a recycle unit, and a tear line is formed by extending spirally on such anastomotic auxiliary; wherein when pulling such recycle unit, such anastomotic auxiliary is gradually torn into a linear body along such tear line.

The anastomosis set of the fourth example, wherein a metal line is wound onto the anastomotic auxiliary to support it.

The anastomosis set of the fourth example, wherein the anastomotic auxiliary includes a first fusiform half and a second fusiform half, such first fusiform half has a first joint surface mutually joined with a second joint surface of the second fusiform half and in a combined structural form, the first and second fusiform halves having complimentary shaped portions which engage to prevent such first and second fusiform half from mutual slipping during anastomosis, wherein the first joint surface is mutually separated from such second joint surface after anastomosing the body part to be anastomosed, and in a separated structural form to be removed from the body part to be anastomosed.

The anastomosis set of the fourth example, wherein the anastomotic auxiliary has an exit part, and such anastomotic auxiliary is removed from the body part to be anastomosed through such exit part.

The anastomosis set of the fourth example, further comprising an anastomotic auxiliary removal aid, such anastomotic auxiliary removal aid removes the anastomotic auxiliary from the body part to be anastomosed; wherein the anastomotic auxiliary removal aid includes a hollow tube and a removal device; wherein the hollow tube has an access in which such removal device locates; and such removal device connects such anastomotic auxiliary.

The anastomosis set of the fourth example, further comprising an anastomotic auxiliary removal aid, such anastomotic auxiliary removal aid removes the anastomotic auxiliary from the body part to be anastomosed; wherein the anastomotic auxiliary removal aid includes an arcuate sheet component and a removal device; wherein the arcuate sheet component has a removal hole, through which such removal device connects such anastomotic auxiliary.

All aspects mentioned above and other aspects of this Invention will be clearer according to the following unrestricted detailed descriptions on specific embodiments and by referring to the attached drawings.

BRIEF DESCRIPTION FIG. OF THE DRAWINGS

DETAILED DESCRIPTION

Figure 1A:
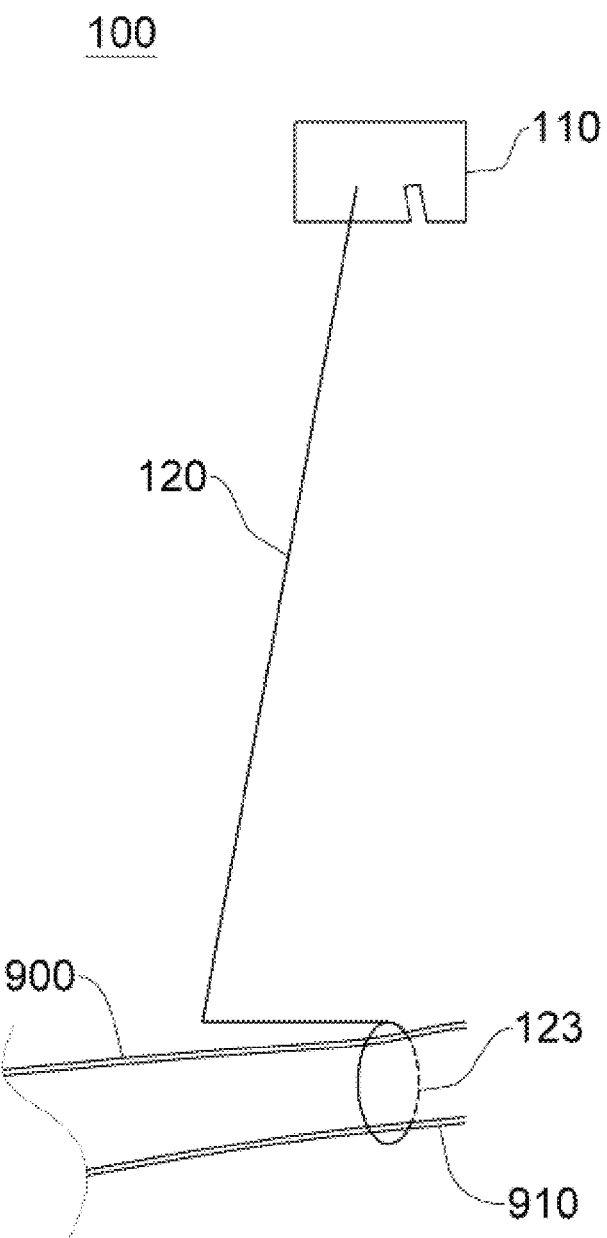
FIGS. 1A-1E is a high-level schematic diagram of an exemplary anastomosis set.

Disclosed herein is an anastomosis set for anastomosing blood vessels, such as arteries or veins. FIGS. 1A-1E depict a high-level example of an anastomosis set 100 showing the general functions of component parts. Anastomosis set 100 is used for anastomosing target vessel 900 to be anastomosed 900, having a first end anastomosed 910 and second end anastomosed 920. According to one example, anastomosis set 100 includes an anastomotic aid device 110; a first manipulator 120; a second manipulator 130; and anastomosis mechanism 140 (FIG. 1C. First manipulator 120 may include a first joint part 121 and a first telescoping part 123; the second manipulator 130 may include a second joint part 131 and a second telescoping part 133. Both the first joint part 121 and second joint part 131 may be jointed to the auxiliary device 110. In a specific embodiment, at least one of the first joint part 121 and the second joint part 131 can be movably attached to the auxiliary device 110 in a manner permitting relative movement between the second joint part 131 and auxiliary device 110. In this way, after jointing, the user may still adjust the first manipulator 120 and/or the second manipulator 130 to align the first end to be anastomosed 910 with the second end to be anastomosed 920. According to another example, the first joint part 121 and/or the second joint part 131 are rigidly jointed to the auxiliary device 110 in a manner without permitting movement of such parts relative to auxiliary device 110. In this example, the ends 910, 920 must be mutually aligned prior to joining the first end 910 to be anastomosed 910 with second end 920.

In a system according to the example illustrated in FIGS. 1A-1E, the first telescoping part 123 is used for telescoping or extending toward first end 910 to be anastomosed of the vessel, and the second telescoping part 133 is used for telescoping or extending toward second end 920 of the target vessel 900. The first manipulator 120 has a first exit part 123A, and the second manipulator 130 has a second exit part 133A. After the target to be anastomosed 900 has been anastomosed, the first manipulator 120 may be removed from the target vessel 900 through the first exit part 123A, and the second manipulator 130 can be removed from the target vessel 900 through the second exit part 133A. In the depicted example, the first exit part 123A is the gap at the first telescoping part 123, and the second exit part 133A is the gap at the second telescoping part 133.

Figure 1B:
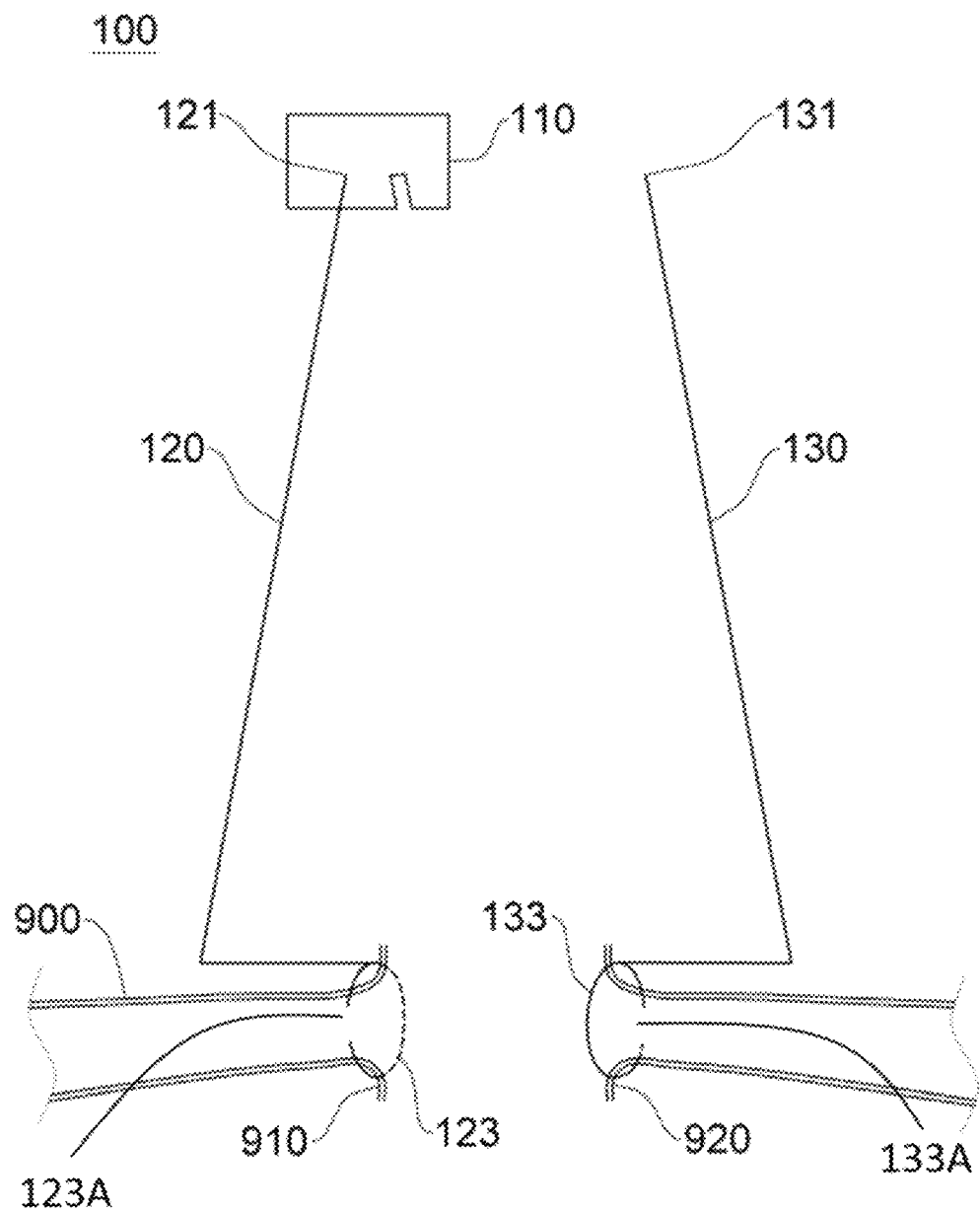
Figure 1C:
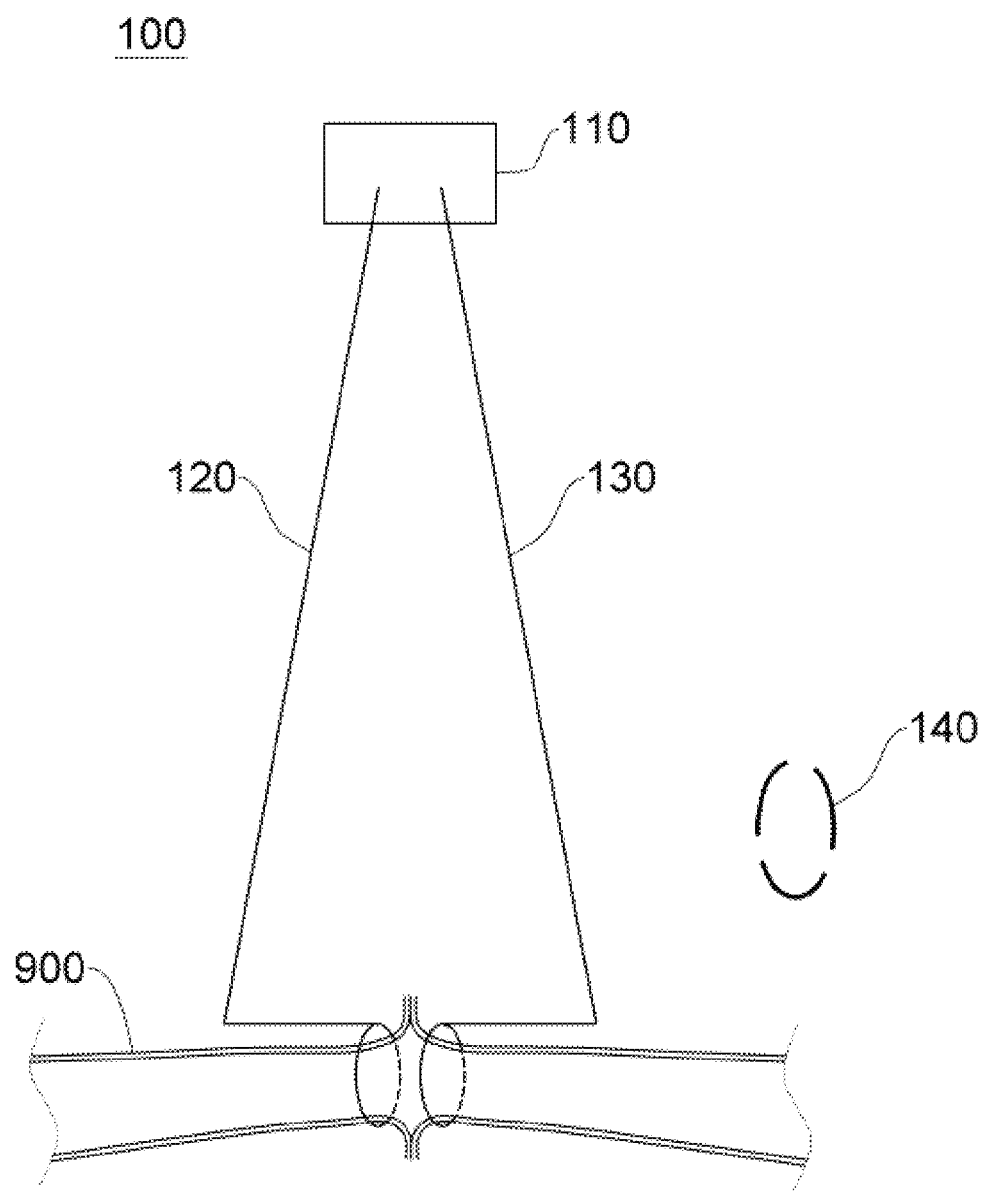
Figure 1D:
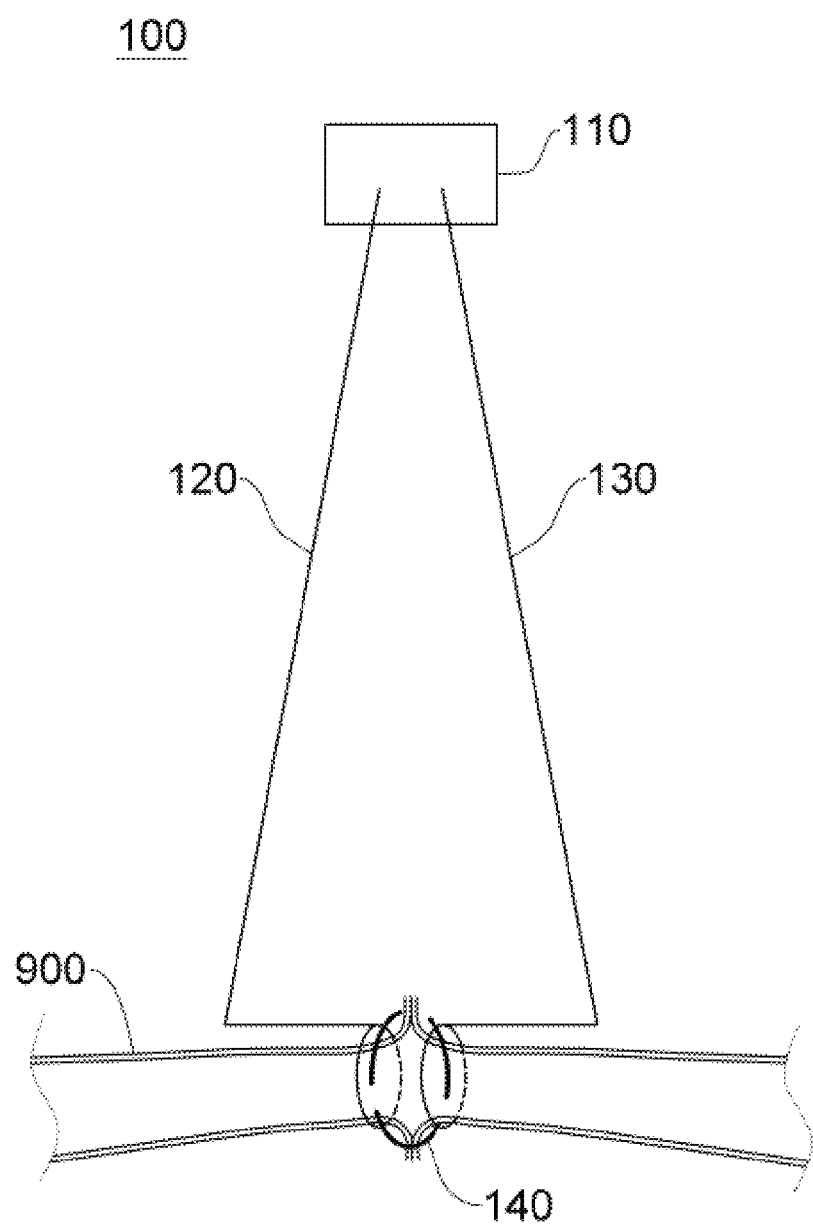
Figure 1E:
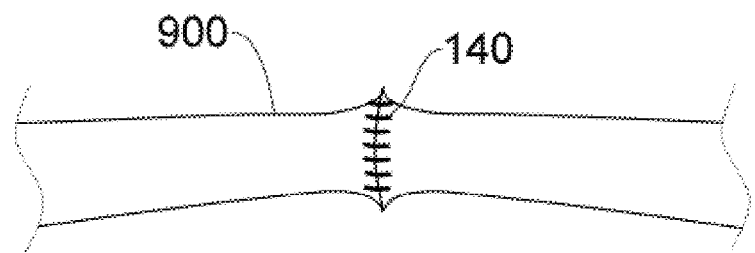
Figure 2A:
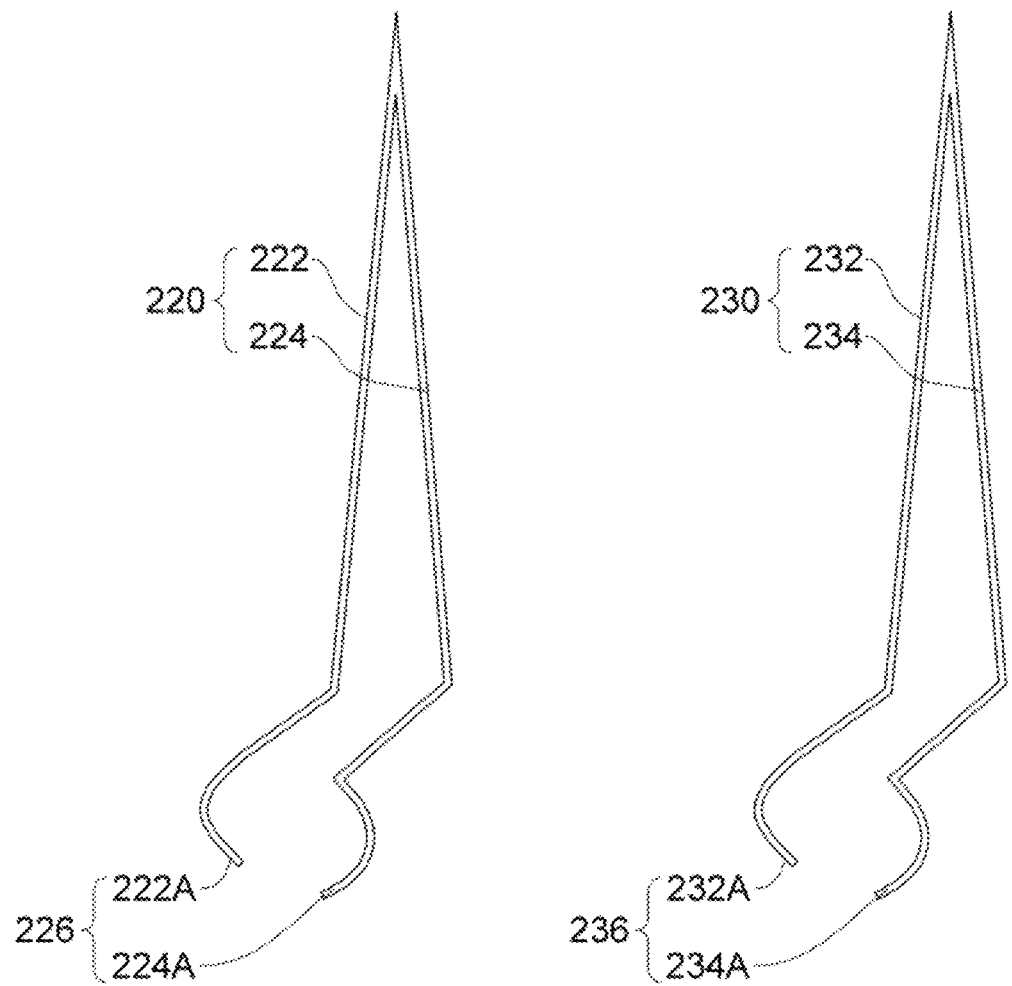
FIGS. 2A-2D is the schematic diagram of a specific embodiment of the first and second manipulator.
Figure 2B:
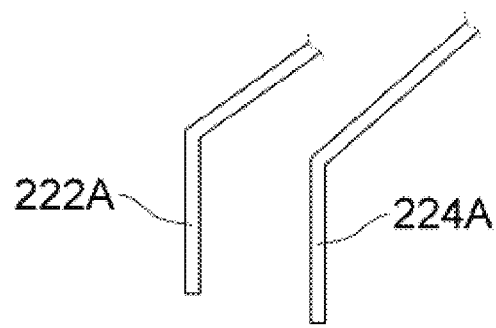
Figure 2C:
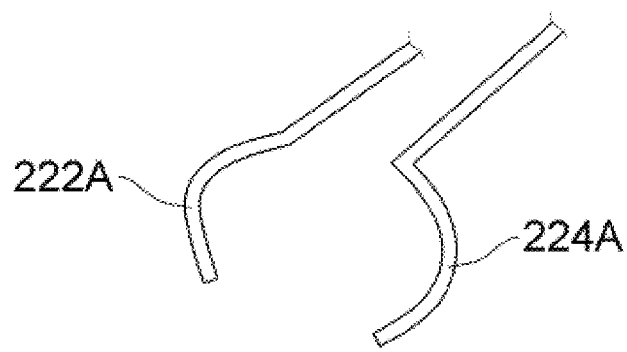
Figure 2D:
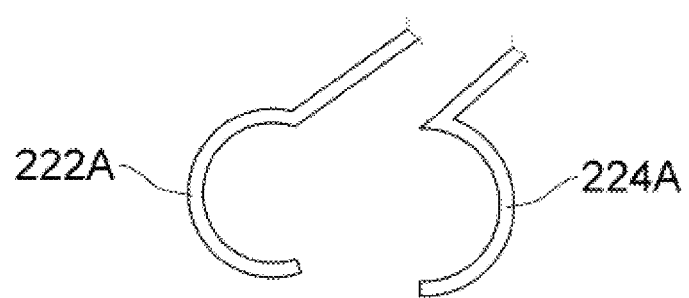

FIG. 2A illustrates aspects of an example first manipulator 220 and second manipulator 220. In some examples, first manipulator 220 may include clamping members 222, 224, and the second manipulator 230 may include clamping members 232, 234. In some examples, clamping members 222, 224 include telescoping portions 222A, 224A. Telescoping portions 222A, 224A cooperatively form the first exit part 226. When the telescoping portions 222A, 224A are separated, the first manipulator 220 can be removed from the target vessel to be anastomosed. Clamping members 232, 234 include telescoping portions 232A, 234A. Telescoping portions 232A, 234A cooperatively form the second exit part 236. When the telescoping portions 232A, 234A are separated, the second manipulator 230 can be removed from the target vessel to be anastomosed. In FIG. 2A, proximal ends of clamping members 222 and 224 are mutually connected, and proximal ends of clamping half 232 and 234 are mutually connected. In some examples, the first manipulator 220 includes a first fixing device used for fixing or locking clamping portions 222, 224 to each other. After fixing or locking the clamping portions 222, 224, the first manipulator 220 resembles the first manipulator 120 depicted in FIGS. 1A-1E. In some examples, second manipulator 230 has the second fixing device or lock BB used for fixing or locking clamping portions 232, 234 to each other. After fixing or locking the clamping portions 232, 234, the first manipulator 220 and the second manipulator 230 resemble the first manipulator 120 and the second manipulator 130 respectively as shown in FIGS. 1A-1E. FIGS. 2B-2D examples of telescoping portions 222A, 224A, 232A, and 234A.

Referring to FIG. 1A, when using anastomosis set 100, the first manipulator 120 may be connected to the auxiliary device 110, and then the telescoping part 123 of the first manipulator 120 is telescoped or extended toward the first end 910 of the target to be anastomosed 900. In some examples, the first manipulator 120 may not be attached or connected to the auxiliary device 110 until after the first manipulator 120 is telescoped or extended toward the first end 910.

Referring to FIG. 1B, after the first telescoping part 123 of the first manipulator 120 has been extended or telescoped toward the first end 910, the second telescoping part 133 of the second manipulator 130 may be telescoped or extended toward the second end 920. In some examples, ends 910 and 920 of the target vessel 900 are folded toward the first telescoping part 123 and second telescoping part 133, respectively, prior to the aforementioned extending or telescoping. The method of folding the end of target to be anastomosed 900 to telescoping part may be the method as shown in Taiwan Patent Application No. 101144007, but not limited to this. Taiwan Patent Application 101144007 is incorporated into this article by reference. Please be aware that, the folding mentioned above may be full folding outward (folding at 180 degree) or half folding outward (folding at 45 to 90 degree), but the invention is not limited to this. An Arterial Everter developed by the University of Michigan may be used to assist in folding the first end to be anastomosed 910 or second end to be anastomosed 920 of the target to be anastomosed 900.

Referring to FIG. 1C, after the first end to be anastomosed 910 and second end to be anastomosed 920 of the target to be anastomosed 900 have been folded to the first telescoping part 123 and second telescoping part 133, the second manipulator 130 may be attached or coupled to the auxiliary device 110. Please note that, if the first manipulator 120 is not already attached or coupled to the auxiliary device 110, the first manipulator 120 may be attached or coupled to the auxiliary device 110 at this moment. Then, auxiliary device 110 may be used to align the first end to be anastomosed 910 with the second end to be anastomosed 920 using the first manipulator 120 and second manipulator 130.

Figure 3A:
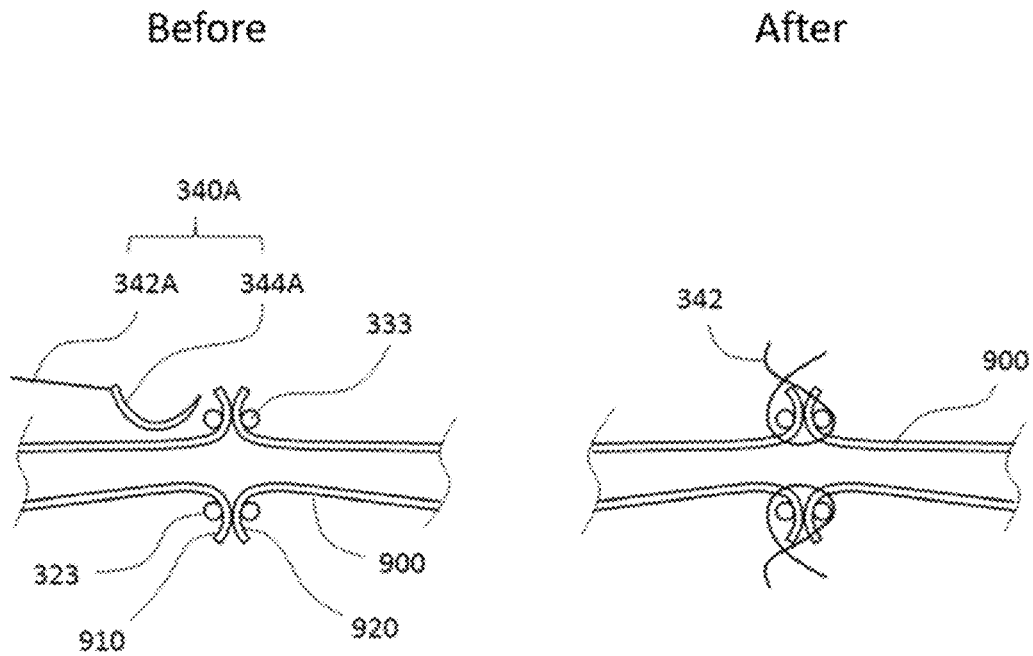
FIGS. 3A-3E is the schematic diagram of a specific embodiment of anastomosis mechanism.
Figure 3B:
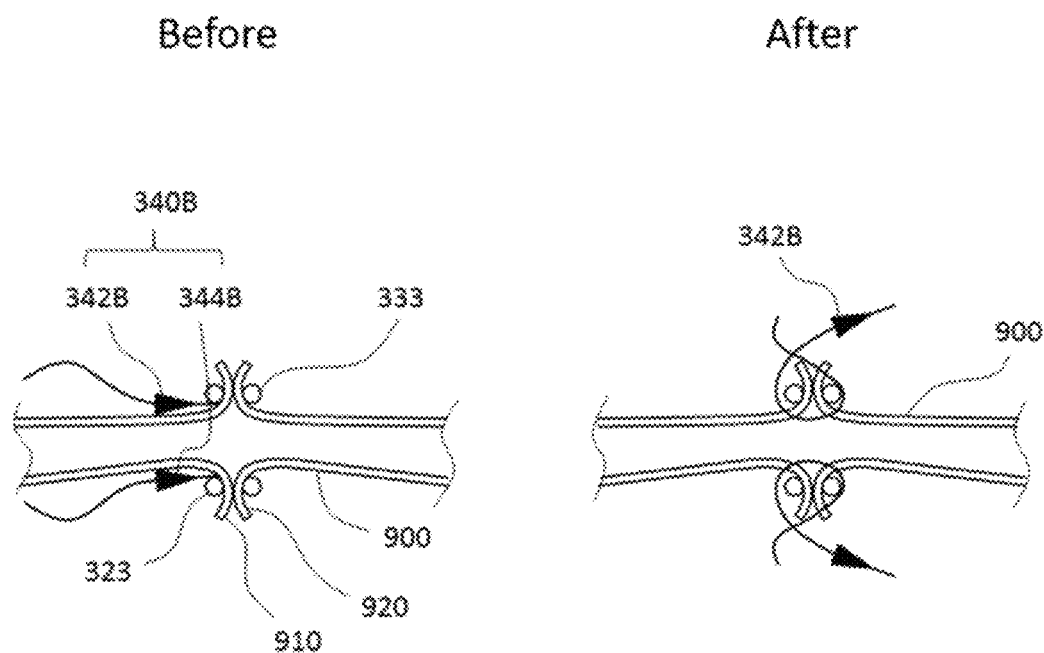

Referring to FIG. 1D, after the first end to be anastomosed 910 and second end to be anastomosed 920 have been mutually aligned to each other, an anastomosis mechanism 340 may be used to anastomose the first end to be anastomosed 910 with the second end to be anastomosed 920 of the target. FIGS. 3A-3E illustrate exemplary anastomosis mechanisms 340 and methods of anastomosis. In the example shown in FIG. 3A, anastomosis mechanism 340A includes suture line 342A and suture needle 344A. After the first end to be anastomosed 910 has been mutually aligned with the second end to be anastomosed 920 using first telescoping part 323 and the second telescoping part 333, use the suture line 342A and suture needle 344A to suture together the first end 910 and the second end 920. As shown in FIG. 3B, the anastomosis mechanism 340B includes the first suturing instrument 342B and the second suturing instrument 344B. After the first end 910 has been mutually aligned to the second end 920 using the first telescoping part 323 and the second telescoping part 333, use the first suturing instrument 342B and second suturing instrument 344B to suture together the first end 910 and the second end 920. In some examples, the anastomosis mechanism 340B may only include one suturing instrument.

Figure 3C:
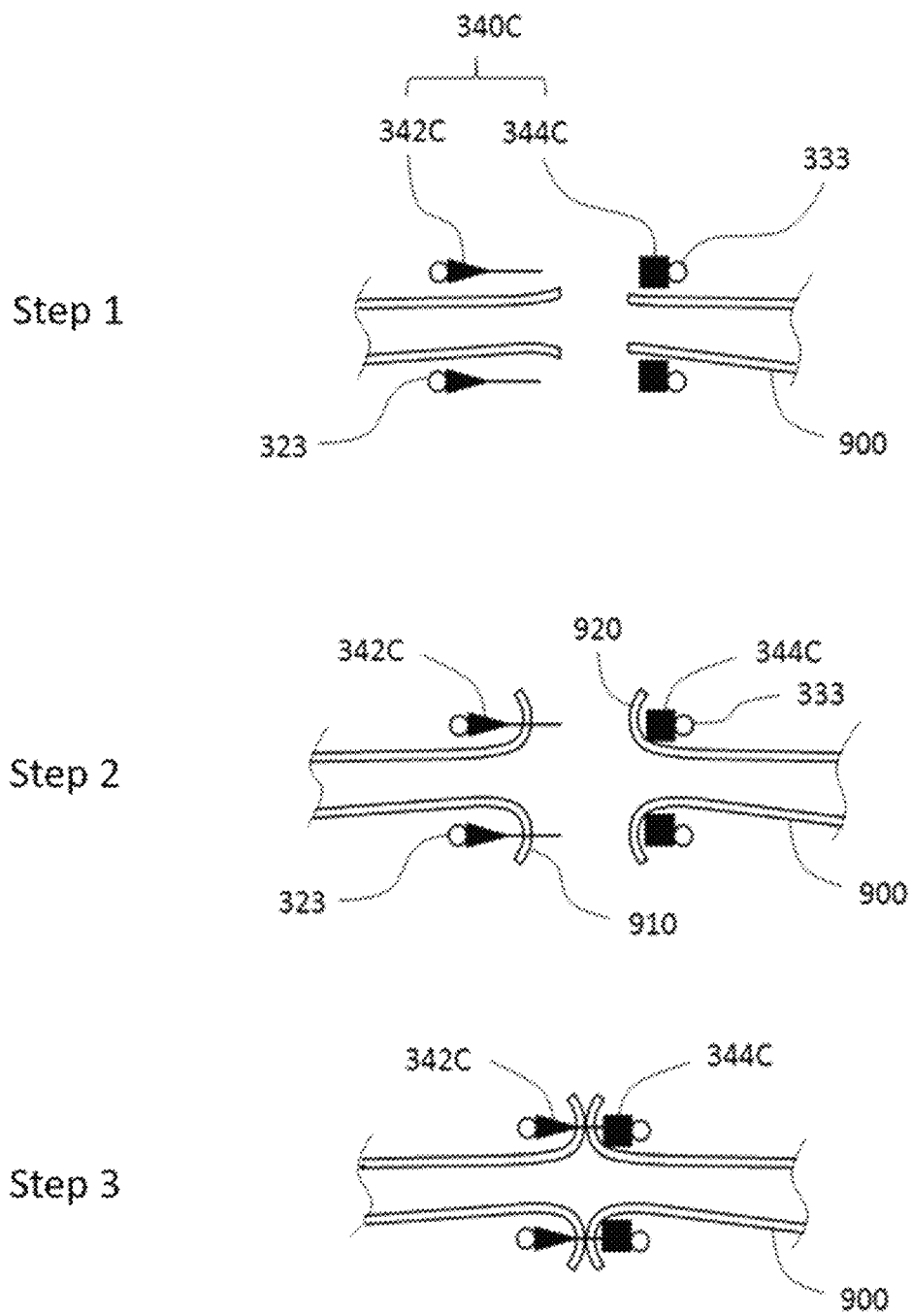
Figure 3D:
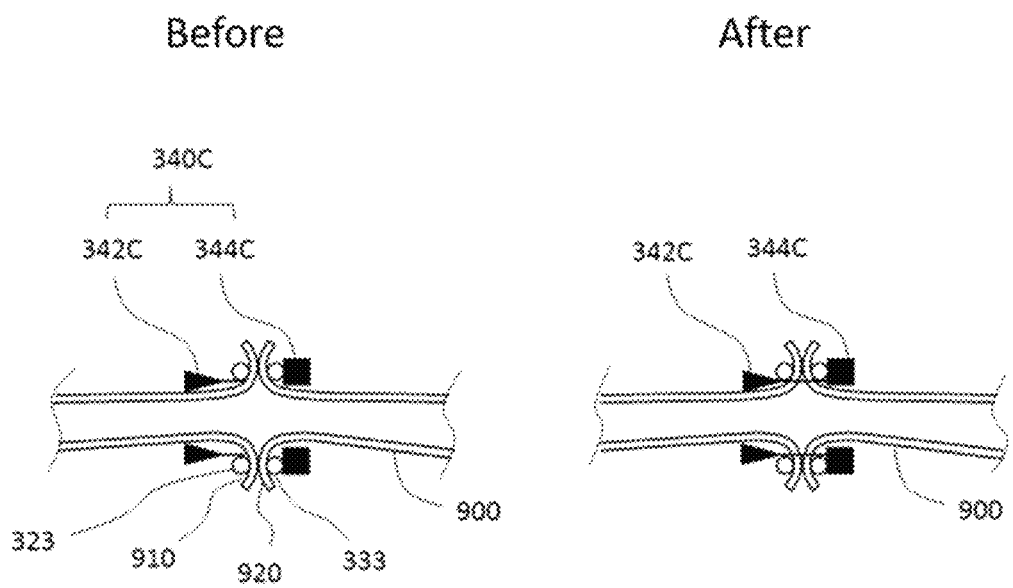

Referring to FIG. 3C, anastomosis mechanism 340C includes a first anastomotic device 342C and a second anastomotic device 344C. In some examples, the first anastomotic device 342C equipped with one or more coupling pins. In the course of anastomosing, fix the first anastomotic device 342C between the first telescoping part 323 and the first end 910, at this moment, the coupling pin of the first anastomotic device 342C pierces through the first end 910. Next, position the second anastomotic device 344C between the second telescoping part 333 and the second end 920. The first telescoping part 323 and/or second telescoping part 333 are then pushed in together in order to approximate the first anastomotic device 342C and the second anastomotic device 344C. This case the coupling pin of the first anastomotic device 342C to pierce through the second end to be anastomosed 920 and couple with the second anastomotic device 344C to complete the anastomosis. FIG. 3D illustrates another way of using the anastomosis mechanism 340C. As shown in the embodiment of FIG. 3D, after the first end to be anastomosed 910 and second end to be anastomosed 920 have been mutually aligned, the coupling pin of the first anastomotic device 342C is advanced through the first end to be anastomosed 910 and second end to be anastomosed 920, coupling the first anastomotic device 342C with the second anastomotic device 344C thereby completing the anastomosis. In some examples, after finishing anastomosing using the anastomosis mechanism 340C, the anastomosis mechanism 340C may remain in the target vessel 900 as an implant.

Figure 3E:
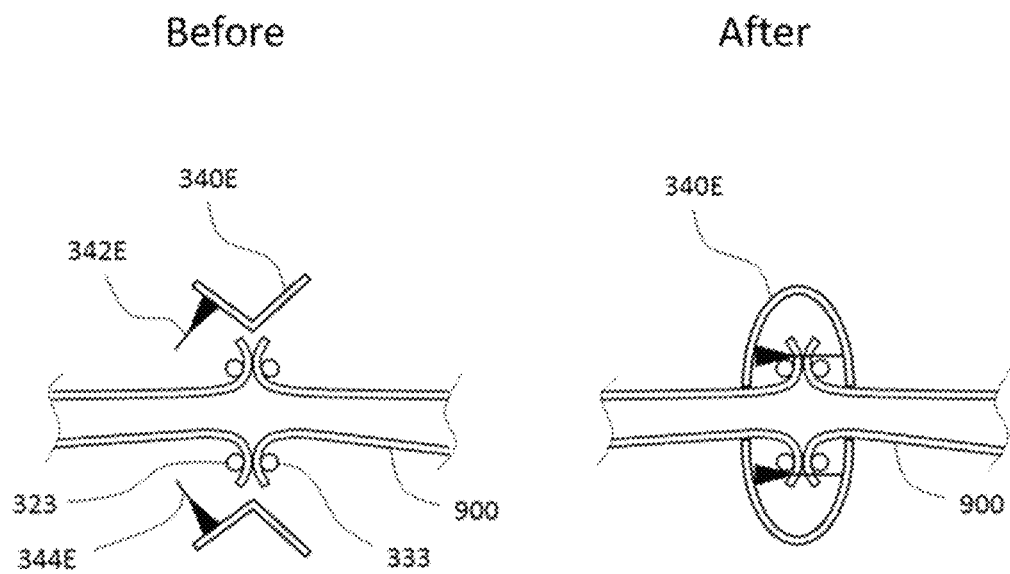

Referring to FIG. 3E, an exemplary anastomosis mechanism 340E is depicted as a bendable clamping mechanism. One end of the anastomosis mechanism 340E has plural coupling pins 342E and 344E. In the course of anastomosing using anastomosis mechanism 340E, advance the coupling pin 342E to pierce through the first end to be anastomosed 910 and second end to be anastomosed 920, and couple with the other end of anastomosis mechanism 340E to finish anastomosing. According to one example, the anastomosis mechanism 340E mutually clamps together the first end to be anastomosed 910 and second end to be anastomosed 920.

It should be noted that the anastomosis mechanisms shown in FIGS. 3A-3E are only provided as examples and that different types of anastomosis mechanisms may be used as needed. For example, anastomosis mechanisms of suturing type, buckling type, clamping type, nailing type or bonding type may be used, but the invention is not limited to this. According to one example, the AnastoClip® VCS Closure System is used as the anastomosis mechanism. In some examples using VCS Closure System as the anastomosis mechanism to anastomose the vein, the opening width of the clips of VCS Closure System may fall between 0.9 mm and 1.4 mm before closing, but the invention is not limited to this. In other examples using VCS Closure System as the anastomosis mechanism to anastomose artery, the opening width of the clips of VCS Closure System may fall between 1.4 mm and 2.5 mm before closing, the invention is not limited to this.

Referring back to FIG. 1E, after anastomosing the first end to be anastomosed 910 and second end to be anastomosed 920 of the target to be anastomosed 900, remove the first manipulator 120 and second manipulator 130 from the target to be anastomosed 900 through the first and second exit parts 123A, 133A, respectively.

FIGS. 4A-4H, illustrate an exemplary anastomosis set 400 including a first manipulator 420, a second manipulator 430, the anastomosis mechanism 440, anastomotic auxiliary 450, and makeup mechanism 460. The first manipulator 420 has the first telescoping part 423, the second manipulator 430 has the second telescoping part 433, and the anastomotic auxiliary 450 has the exit part 452. According to one example, the anastomotic auxiliary 450 is flexible. In some examples, the anastomotic auxiliary 450 may contain a liquid or a fluid (such as buffered saline) or a gas. The anastomotic auxiliary 450 may be formed of an elastomer (such as balloon, silica gel containing liquid and/or gas, which cannot be broken easily), or may be the solid elastomer (such as silica gel) or shape memory metal (nickel-titanium alloy), but not limited to this.

Figure 5A:
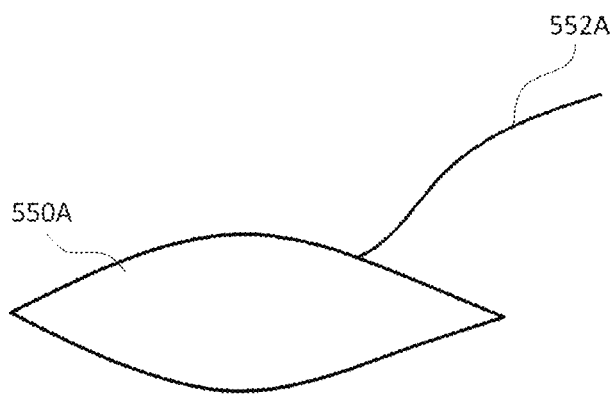
FIGS. 5A-5B is the schematic diagram of a specific embodiment of anastomotic auxiliary.

FIGS. 5A, 5B and FIGS. 6A-6E describe exemplary anastomotic auxiliary 550A, 550B, and 650. As shown in the example of FIG. 5A, the interior of anastomotic auxiliary 550A may be hollow. The anastomotic auxiliary 550A may be deformable, which may facilitate embedding the anastomotic auxiliary 550A into the target to be anastomosed or withdraw from it. The anastomotic auxiliary 550A has the exit part 552A (in some examples, the anastomotic auxiliary exit part 552A may be a line), user may remove the anastomotic auxiliary 550A from the target to be anastomosed by pulling the exit part 552A. In some examples, the anastomotic auxiliary 550A is closed, and its internal gas or liquid cannot be supplemented or released at any time. In other examples, the anastomotic auxiliary 550A may have an opening-closing hole or a valve, so that user may supplement or release the gas or liquid inside the anastomotic auxiliary 550A through an opening-closing hole or valve at any time. For example, before embedding the anastomotic auxiliary 550A into the target to be anastomosed, user may release some of the gas or liquid inside the anastomotic auxiliary 550A through the opening-closing hole or valve first, and then supplement the gas or liquid inside the anastomotic auxiliary 550A through the opening-closing hole or valve after embedding. Before removing the anastomotic auxiliary 550A from the target to be anastomosed, the user may release the gas or liquid inside the anastomotic auxiliary 550A through the opening-closing hole first or valve. It should be understood that the anastomotic auxiliary exit part 552A may not only be situated or located in the middle of anastomotic auxiliary 550A, it may alternatively be located anywhere the anastomotic auxiliary 550A as needed; for example, the anastomotic auxiliary exit part 552A may be set at the end of anastomotic auxiliary 550A.

Figure 5B:
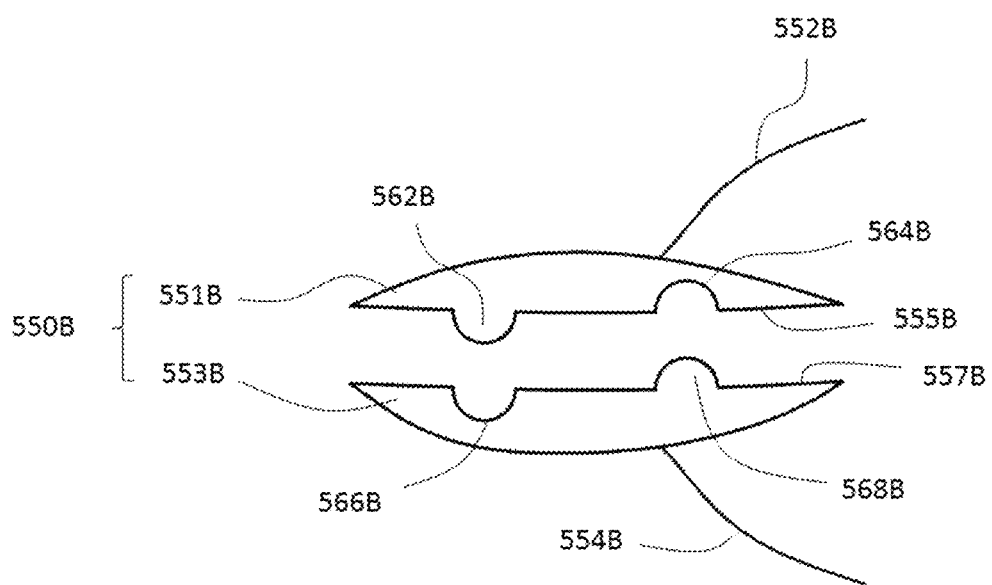

Turning to FIG. 5B, the anastomotic auxiliary 550B includes a first fusiform half 551B and a second fusiform half 553B. A first joint surface 555B of the first fusiform half 551 and the second joint surface 557B of the second fusiform half 553B cooperatively form a fixing mechanism to prevent first fusiform half 551B and second fusiform half 553B from mutual slipping after embedding into the target to be anastomosed. In some examples, the first fusiform half 551B and second fusiform half 553B have the exit part 552B and 554B respectively. The user may remove the first fusiform half 551B and second fusiform half 553B from the target to be anastomosed by pulling the exit parts 552B and 554B, respectively. In some examples, the fixing mechanism is cooperatively formed by concave portions 564B, 566B, convex portions 562B, 568B formed at the first joint surface 555B and second joint surface 557B respectively. The convex portion 562B and concave portion 566B are mutually matched whilst the convex 564B and concave 568B are mutually matched. In some examples, the fixing mechanism is the slight viscosity at the first joint surface 555B and second joint surface 557B. It should be noted that, FIG. 5B is only an example, the anastomotic auxiliary need not only comprise of two fusiform halves, it may include any number of fusiform halves (or fusiform components) as needed. Besides, the first fusiform half exit part 552B and second fusiform half exit part 554B may not only be set in the middle of the first fusiform half 551B and second fusiform half 553B respectively, they may be set at anywhere of first fusiform half 551B and second fusiform half 553B respectively as needed; for example, they may be set at the end of the first fusiform half 551B and second fusiform half 553B respectively.

As shown in the embodiments from FIGS. 6A-6E, the anastomotic auxiliary 650 comprises of plural lines and has the removable auxiliary control units 656 and 658. After the anastomotic auxiliary 650 has been embedded into the target to be anastomosed, the user may control the interval (spacing) between the auxiliary control units 656 and 658 to adjust the tortuosity of the line of anastomotic auxiliary 650, so as to distract the target to be anastomosed. The auxiliary control units 656, 658 may be removed from the anastomotic auxiliary 650 as needed at any time. For example, the auxiliary control units 656 and 658 may be dismantled (removed) from the anastomotic auxiliary 650 before removing the anastomotic auxiliary 650 from the target to be anastomosed. The removal device 674 of anastomotic auxiliary removal aid 670 may be used to fix the anastomotic auxiliary 650. In some examples, the removal device 674 may be connected to the anastomotic auxiliary 650 before embedding the anastomotic auxiliary into the target to be anastomosed. The removal device 674 may be removed from the hollow tube 672 to advance (drive) the anastomotic auxiliary 650 into the hollow tube 672.

Figure 6A:
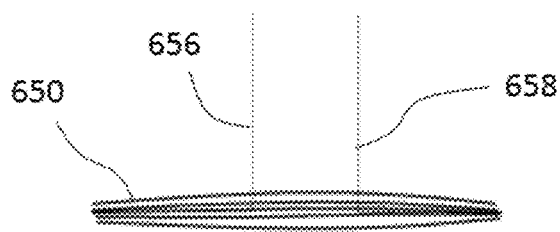
FIGS. 6A-6E is the schematic diagram of a specific embodiment of anastomotic auxiliary.
Figure 6B:
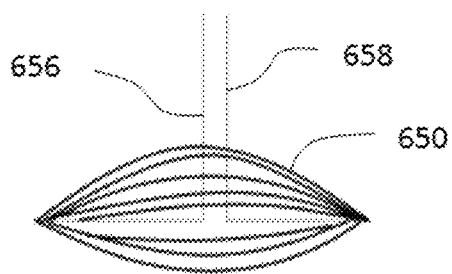
Figure 6C:
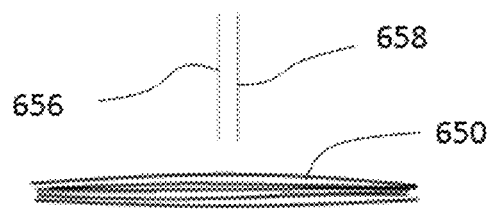
Figure 6:
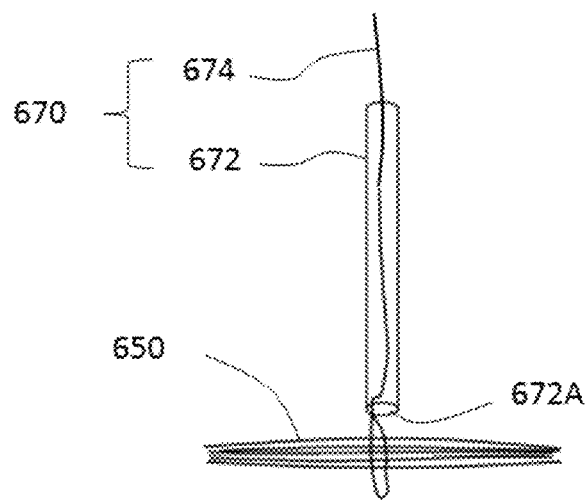
Figure 6E:
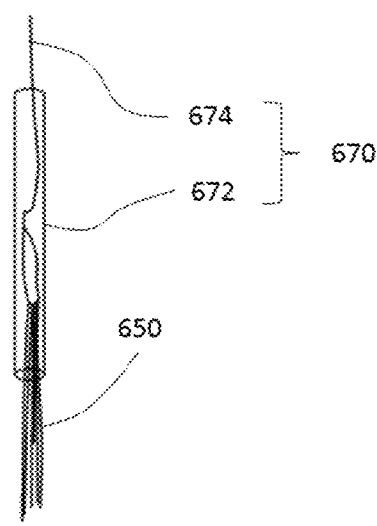

Referring to FIG. 6E, the hollow tube 672 has an access (cutout, port), and the removal device 674 is at least partially housed within the hollow tube 672. In some examples, the tube diameter of the front end 672A of hollow tube 672 is slightly smaller than the pore diameter of the un-anastomosed gap to be anastomosed. Using a slightly smaller diameter of the front end 672A of hollow tube 672 can avoid the anastomotic auxiliary from enlarging the pore diameter of un-anastomosed gap. In other examples, the tube diameter of the front end 672A of hollow tube 672 substantially equals to the pore diameter of the un-anastomosed gap, or is only slightly larger than the pore diameter of the un-anastomosed gap.

Referring once again to FIGS. 4A-4H, the first telescoping part 423 may be used for extending toward the first end to be anastomosed 910, and the second telescoping part 433 may be used for extending toward the second end to be anastomosed 920. In some examples, the first manipulator 420 has a first exit part, and the second manipulator 430 has a second exit part. After the target to be anastomosed 900 has been anastomosed, the first manipulator 420 can be removed from the target to be anastomosed 900 through the first exit part, and the second manipulator 430 can be removed from the target to be anastomosed 900 through the second exit part. In some examples, the first exit part is the gap at the first telescoping part 423, and the second exit part is the gap at the second telescoping part 433. In some examples, the structure of the first manipulator 423 and second manipulator 433 may be as shown from FIG. 2A to FIG. 2D.

Figure 4A:
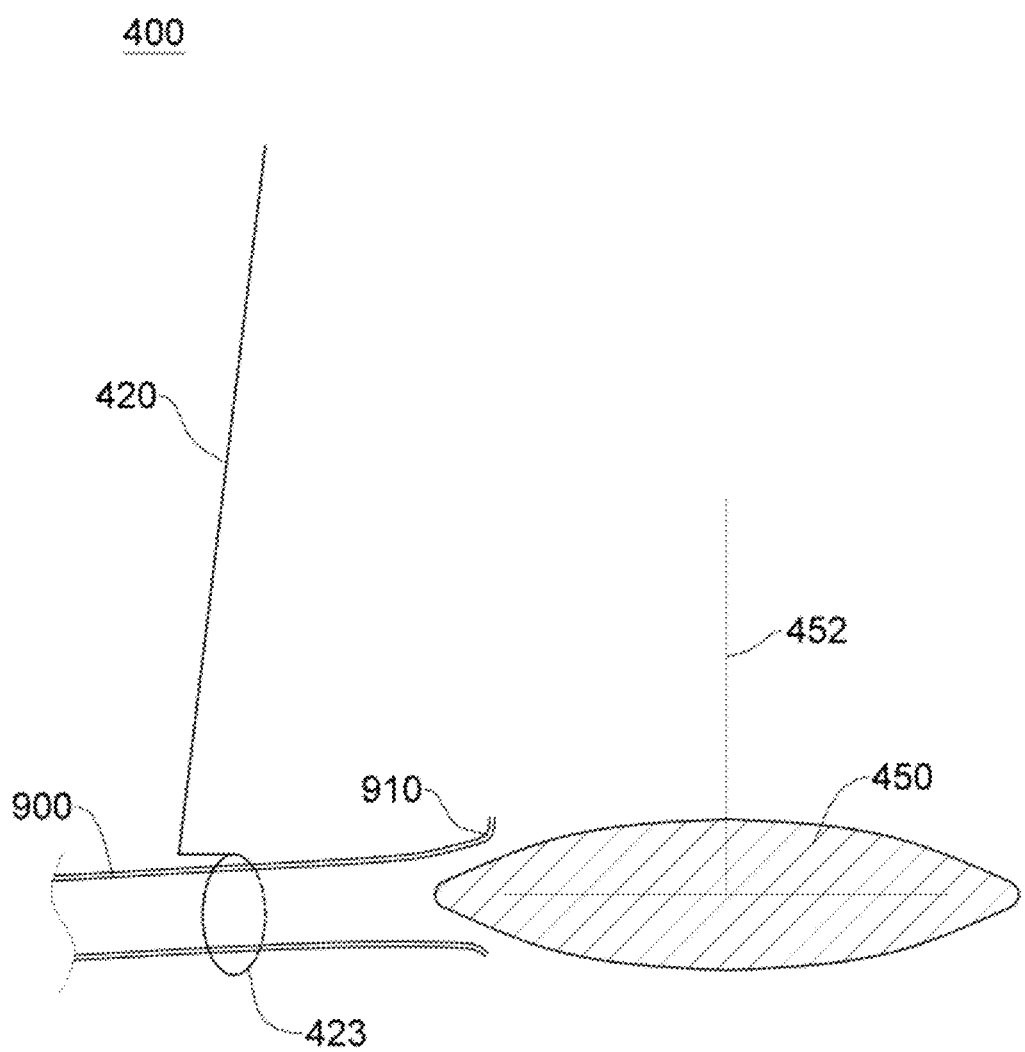
FIGS. 4A-4H is the application schematic diagram of a specific embodiment of anastomosis set in this Invention.
Figure 4B:
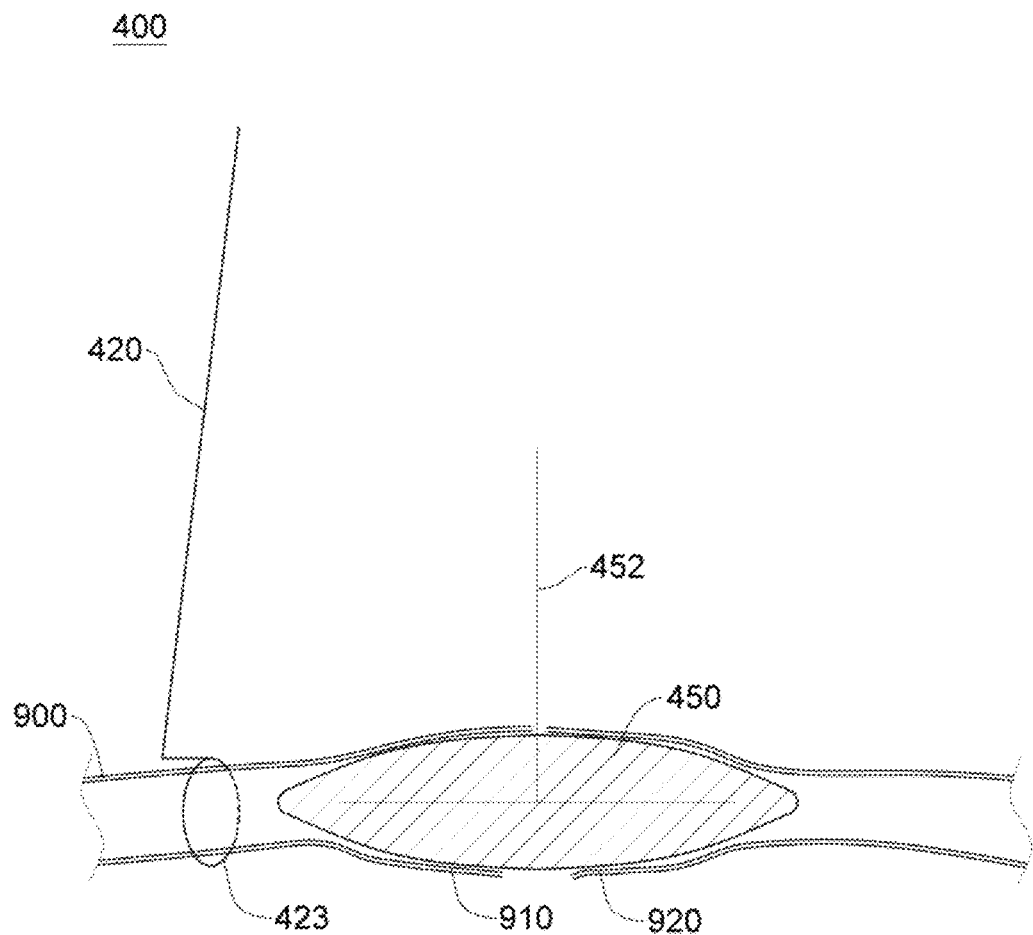

Referring to FIG. 4A, when using the anastomosis set 400, telescope the first telescoping part 423 of the first manipulator 420 toward the first end to be anastomosed 910, and then make one end of anastomotic auxiliary 450 enter from the first end to be anastomosed 910. Then, as shown in FIG. 4B, make another end of anastomotic auxiliary 450 enter from the second end to be anastomosed 920.

Figure 4C:
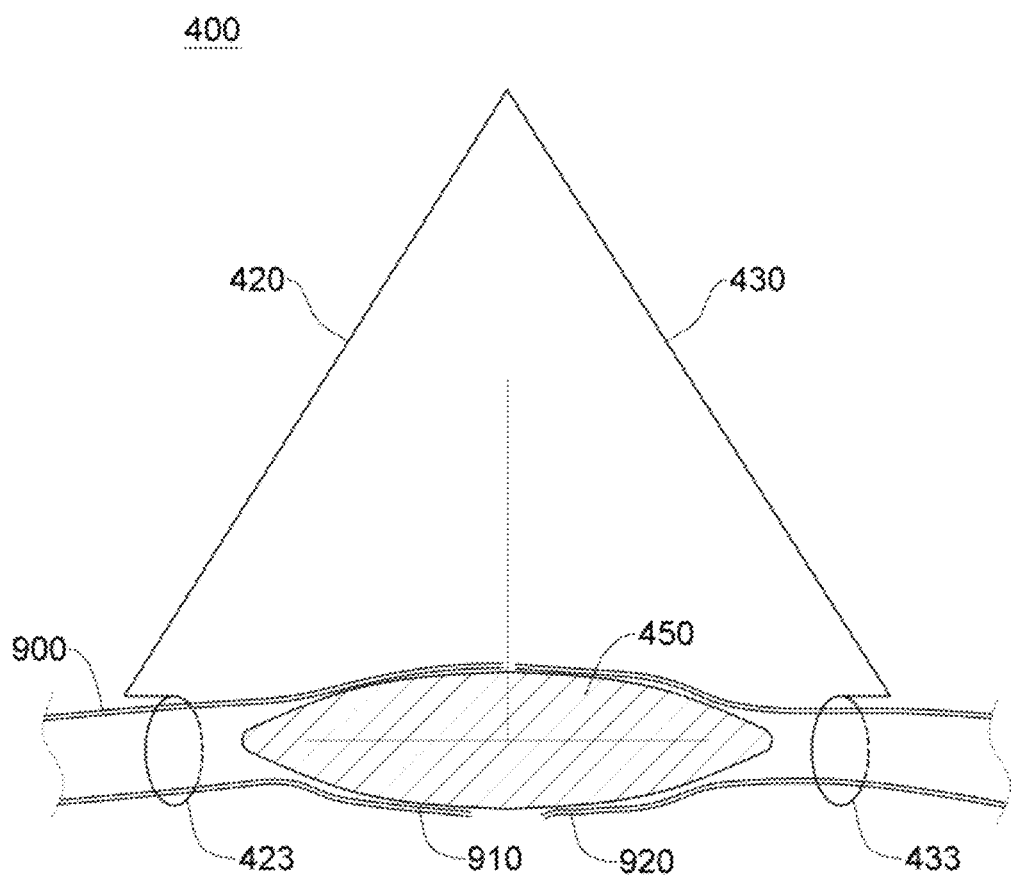
Figure 4D:
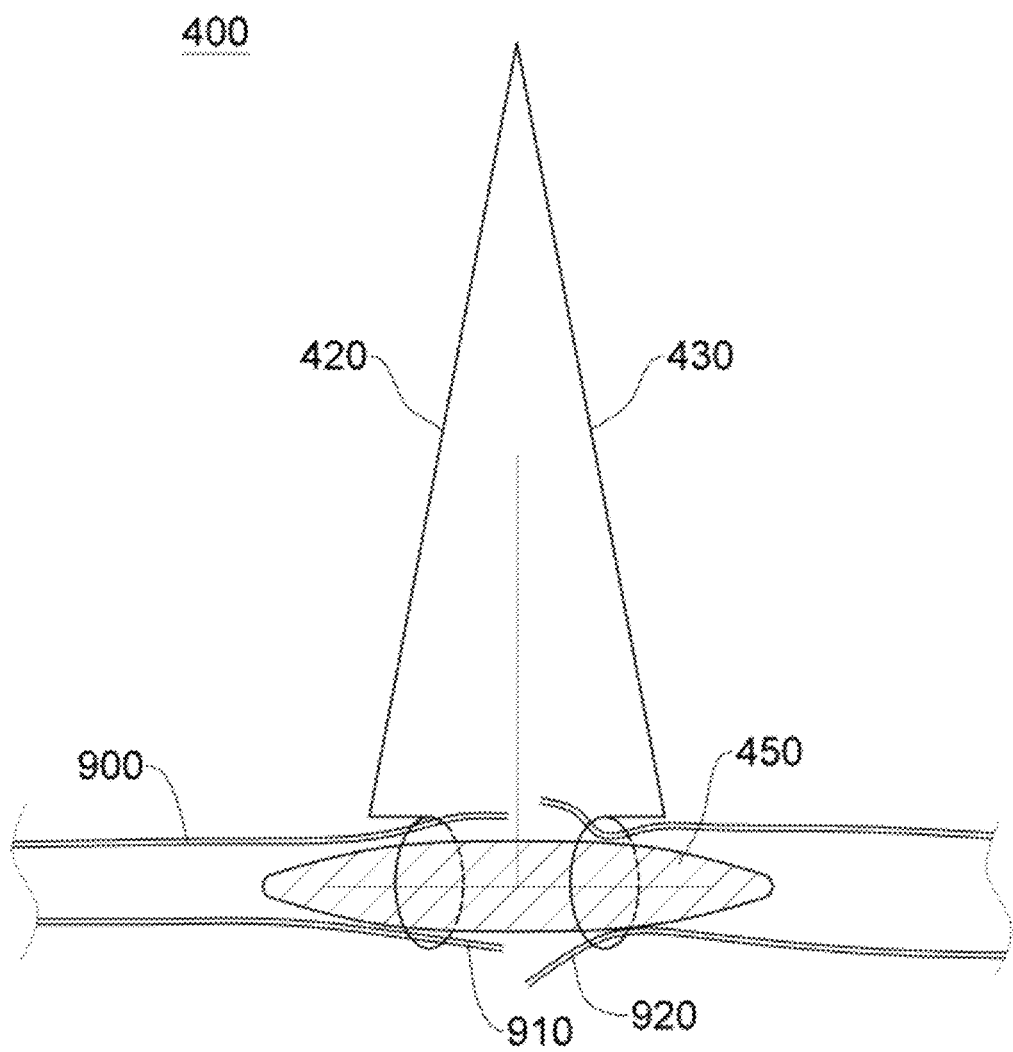
Figure 4E:
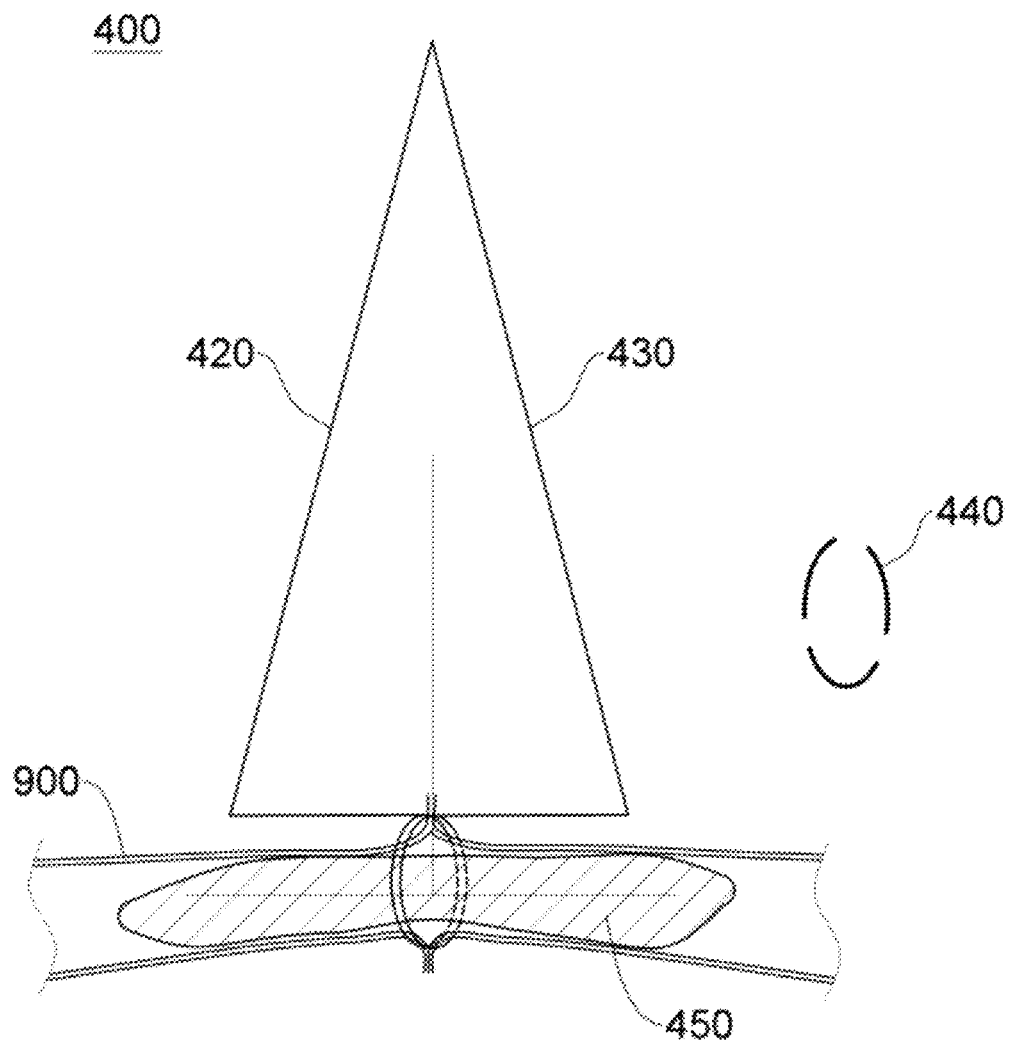

Referring to FIG. 4C, after another end of the anastomotic auxiliary has entered from the second end to be anastomosed 920 through the second exit part of the second manipulator 430, telescope the second telescoping part 433 of the second manipulator 430 to the second end to be anastomosed 920. Referring to FIGS. 4D and 4E, the first end to be anastomosed 910 and second end to be anastomosed 920 are approximated and aligned by approximating the first manipulator 420 and the second manipulator 430. In one example, the proximal ends of the first and second manipulator 420, 430 are mutually connected for the convenience of operation. In other examples, the anastomosis set 400 may include the anastomotic aid device as shown in FIGS. 1A-1D, which may assist the proceeding of anastomosis. In some examples, the first telescoping part 423 is advanced (extended, telescoped) toward the first end to be anastomosed 910, the first end 910 should be folded, and the second telescoping part 433 is advanced (extended, telescoped) to the second end to be anastomosed 920 and end 920 should be folded. In this way, it can avoid the target to be anastomosed 900 from slipping from the first telescoping part 423 or second telescoping part 433.

Figure 4F:
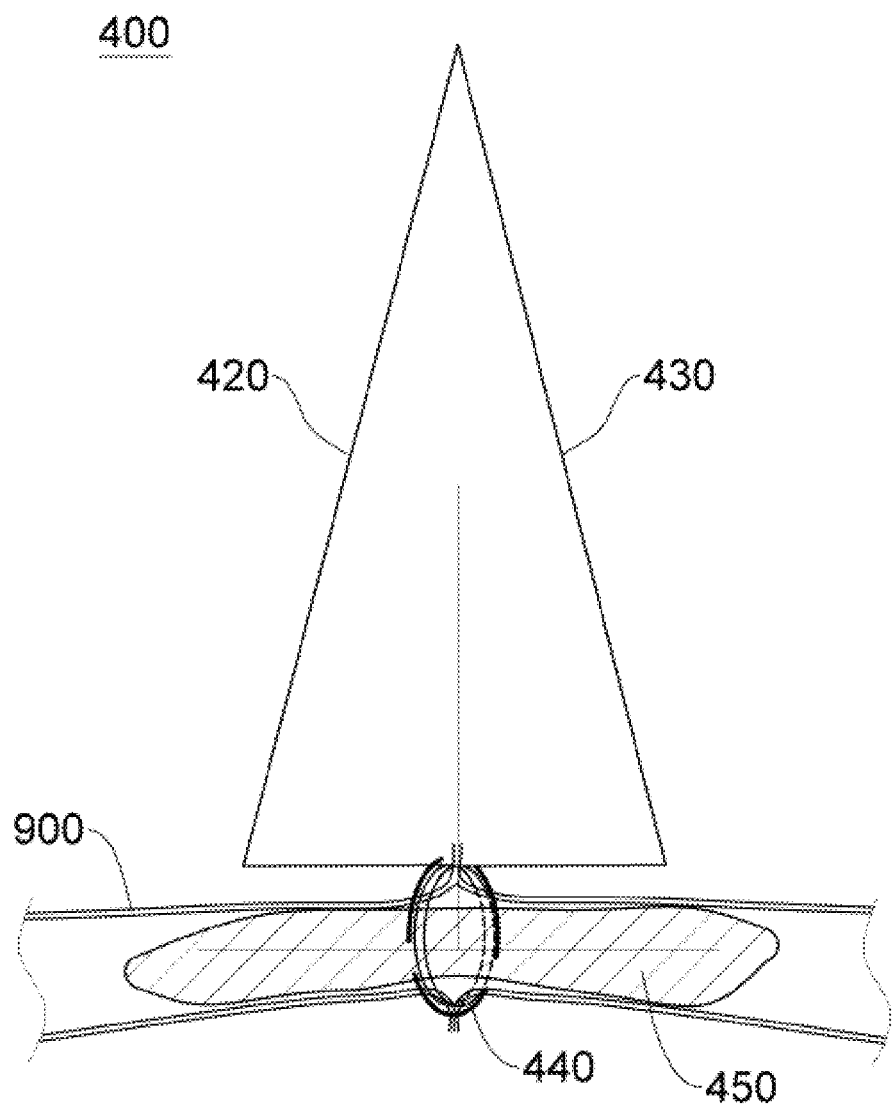

Referring to FIG. 4F, after the first end 910 and second end 920 of the target to be anastomosed 900 have been mutually aligned to each other, use the anastomosis mechanism 440 to anastomose the first end 910 with the second end 920. The anastomosis mechanism and its method may be as described above with reference to FIGS. 3A-3E. It should be noted that, when using the anastomosis mechanism to anastomose the first end 910 with the second end 920 of the target to be anastomosed 900, a certain gap between the first end 910 and the second end 920 needs to be reserved. In other words, total or complete anastomosis is not necessary.

Figure 4G:
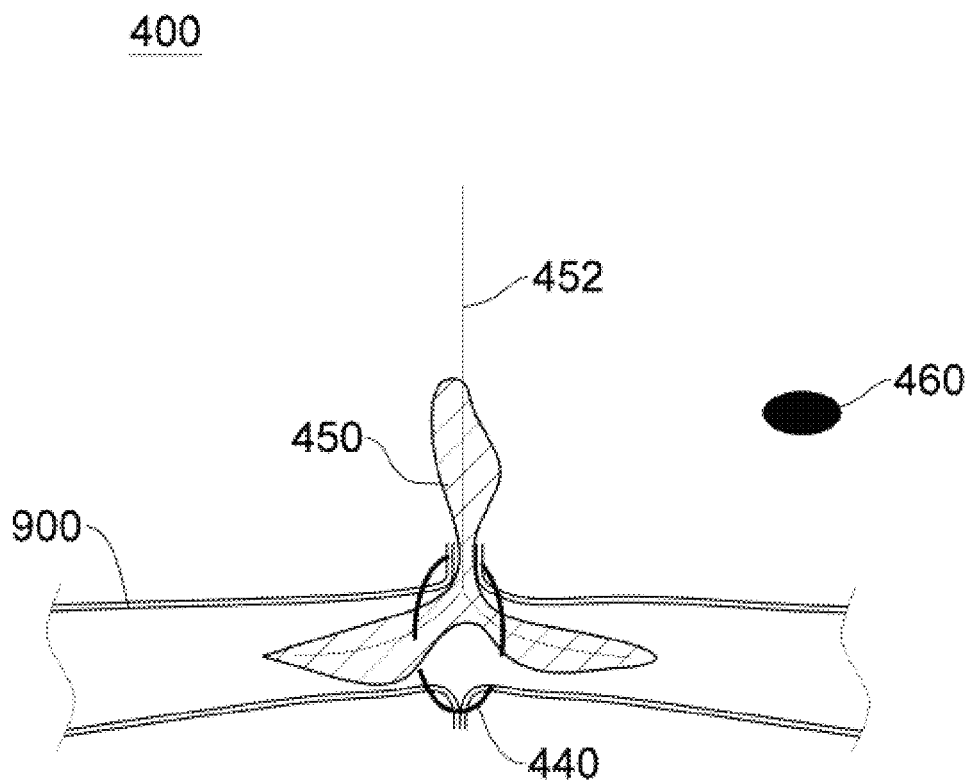
Figure 4H:
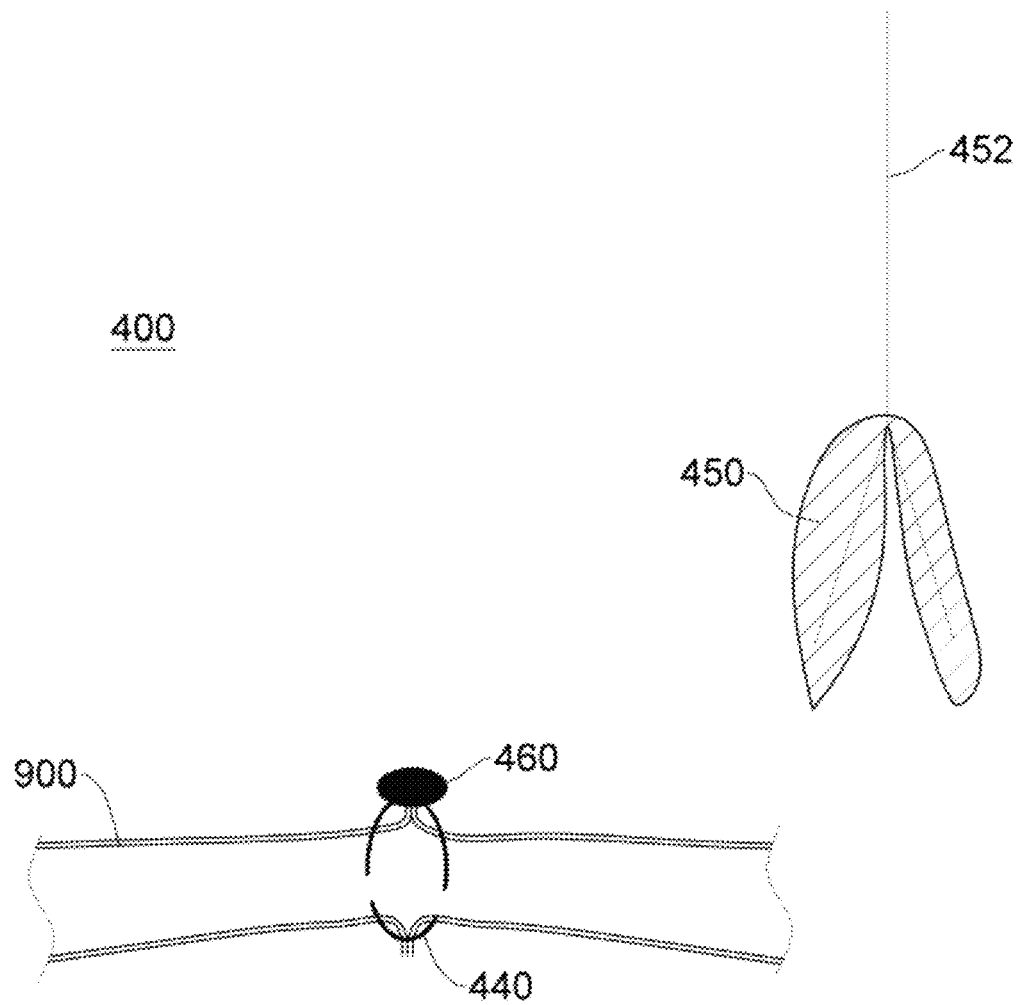

Referring to FIG. 4G, after using the anastomosis mechanism to anastomosed the first end 910 with the second end 920, the anastomotic auxiliary 450 is removed from the anastomosed gap by pushing the anastomotic auxiliary exit part 452, Finally, in FIG. 4H, makeup mechanism 460 is used to make up (complete) the un-anastomosed gap. In different specific embodiments, the makeup mechanism may be, but not limited to, suture mechanism, bonding mechanism, buckling mechanism, clamping mechanism and nailing mechanism etc.

According to one example, anastomotic auxiliary 450 has the hollow tube for drainage of body fluids. In this way, after the first end to be anastomosed 910 and second end to be anastomosed 920 have been mutually aligned to each other, or when using the anastomosis mechanism 440 to anastomose the first end 910 with the second end 920, let the body fluids (e.g. Blood) flow in the hollow tube of anastomotic auxiliary 450, so as to shorten the time of non-flowing body fluids.

Figure 7A:
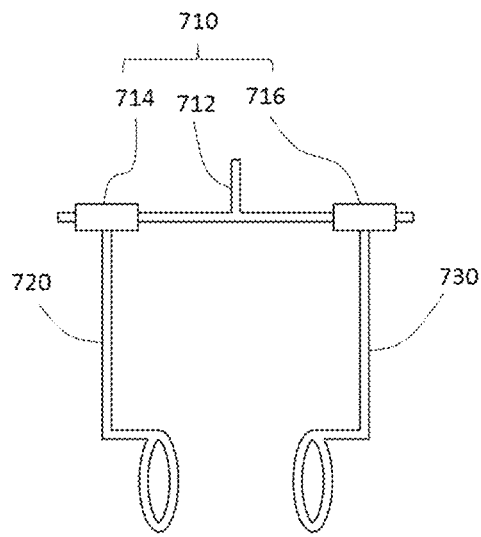
FIGS. 7A-7D is the schematic diagram of a specific embodiment of anastomotic aid device.
Figure 7B:
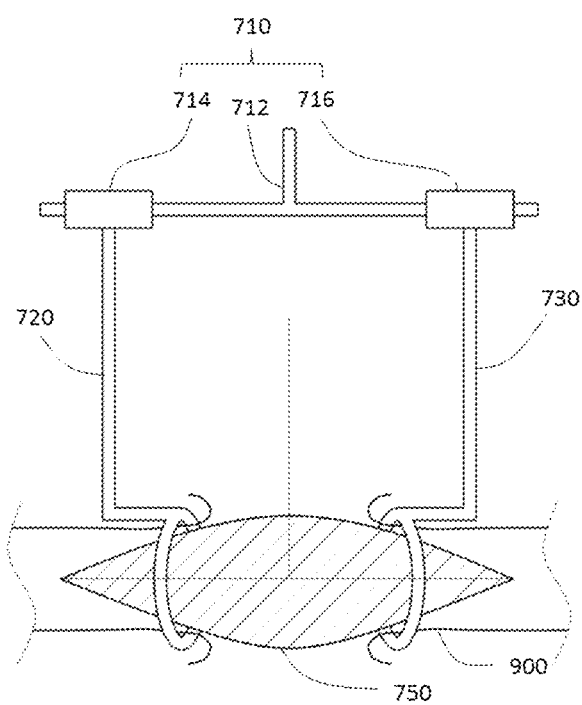

Referring to FIGS. 7A and 7B, the anastomotic aid device 710 includes a main body 712, a first mobile part 714 and a second mobile part 716. The first mobile part 714 and second mobile part 716 can move on (relative to) the main body 712 laterally. Among them, the first mobile part 714 connects to the first manipulator 723, and the second mobile part 716 connects to the second manipulator 730. Thus, the user can move the first mobile part 714 and second mobile part 716 on the main body laterally to assist in anastomosing the target to be anastomosed 900. According to one example, the length of main body 712 is greater than the length of anastomotic auxiliary 750. Please be aware that, the connection method between mobile parts and manipulators may be all-in-one, or it may be connected in a dismountable way.

Figure 7C:
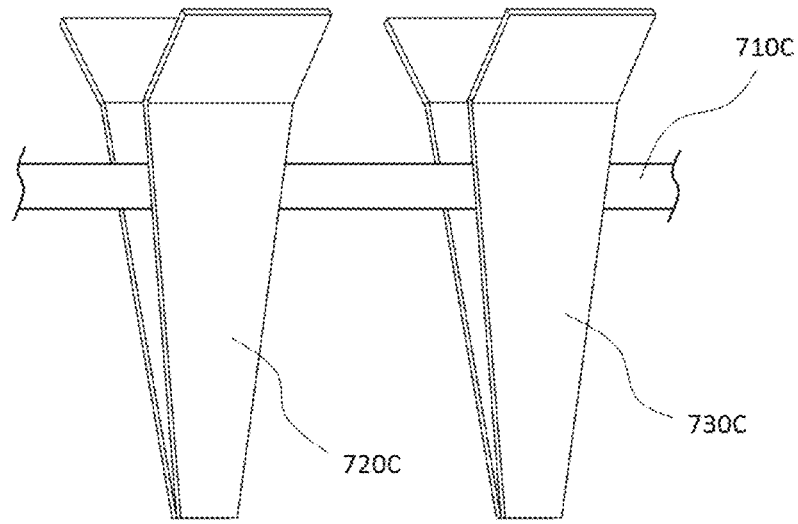

Referring to FIG. 7C, anastomotic aid device 700C includes a main body 710C, a first manipulator 720C and a second manipulator 730C. The first manipulator 720C and the second manipulator 730C can move on the main body 710C laterally. In one example, the anastomotic aid device 700C may further include the first mobile part and second mobile part, which may be set at the main body 710C in a lateral movable way, and the first manipulator 720C and the second manipulator 730C are connected to the first and second mobile part respectively. In accordance with this example, the first manipulator 720C and the second manipulator 730C can move on the main body 710C laterally.

Figure 7D:
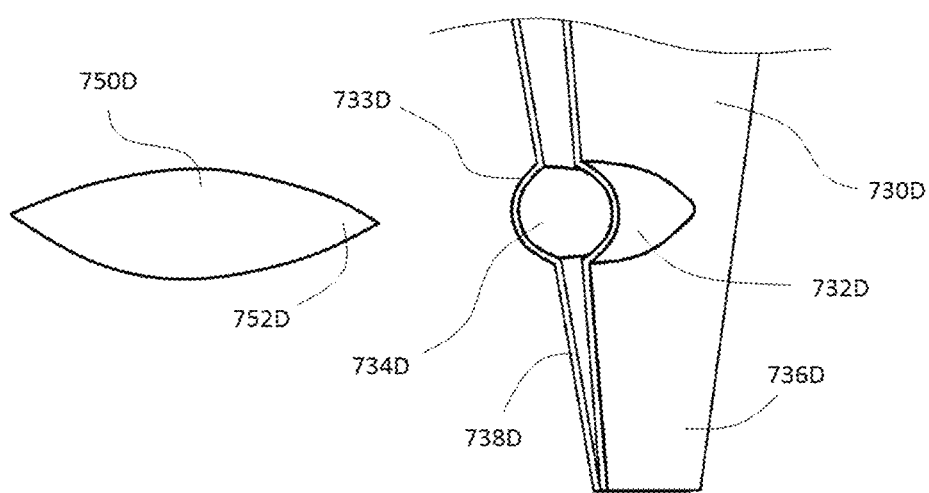

Referring to FIG. 7D, manipulator 730D includes containing parts 732D and 733D. In one example, the shapes of the containing parts 732D and 733D correspond to the shape of end 752D of anastomotic auxiliary 750D. In one example, after the anastomotic auxiliary 750D has entered into the target to be anastomosed, the manipulator 730D is clamped to the target to be anastomosed such that the end 752D of anastomotic auxiliary 750D is contained in the containing parts 732D and 733D. In this way, a part of the anastomotic auxiliary 750D is fixed at the containing space 734D of containing parts 732D and 733D, and further prevents the anastomotic auxiliary 750D from slipping from the manipulator 730D in the course of pushing the manipulator 730D. It should be noted that, FIG. 7D is only one potential example in which the front clamping part 736D and the rear clamping part 738D of the manipulator 730D are closely fitted with each other under clamping status.

Figure 8:
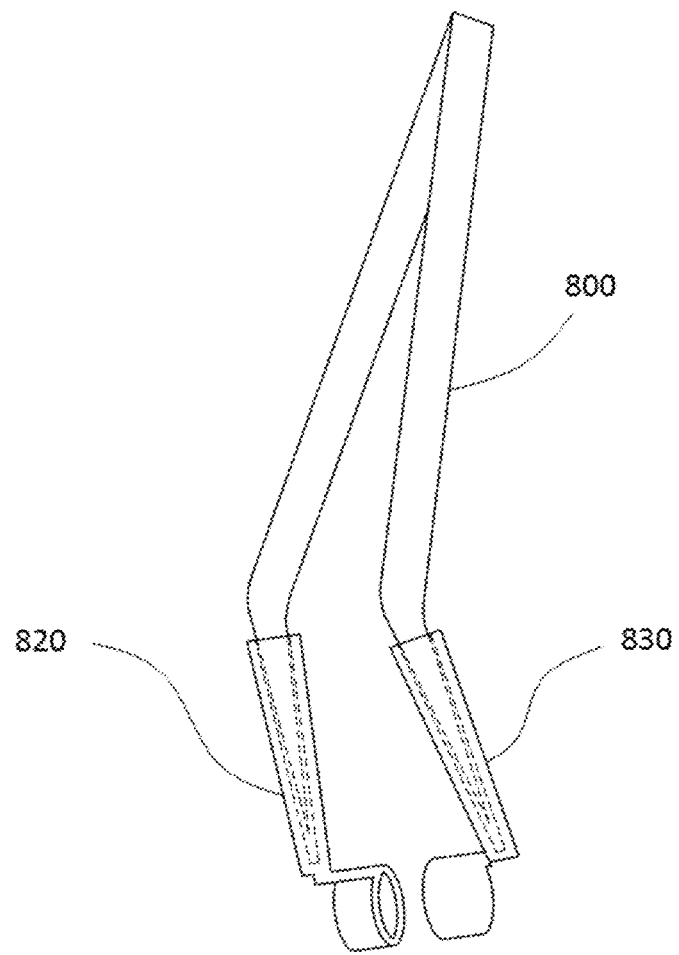
FIG. 8 is the schematic diagram of a specific embodiment of manipulator.

Referring to FIG. 8, first manipulator 820 is set at one end of the clamping device 800 (it is the tweezers in this specific embodiment) in a dismountable way, and the second manipulator 830 is set at the other end of the clamping device 800 in a dismountable way. Please be aware that, both the first manipulator 820 and second manipulator 830 can be set at the clamping device 800 in a dismountable way, hence the user may use different clamping device as needed. For example, the clamping device whose front end is bended at a specific angle may be used, or the clamping device without a bended front end may be used. The user may use the first manipulator 820 and second manipulator 830 in conjunction with other devices as needed. For example, the first manipulator 820 and second manipulator 830 may be used in conjunction with a longilineal (elongate) medical device.

Figure 9A:
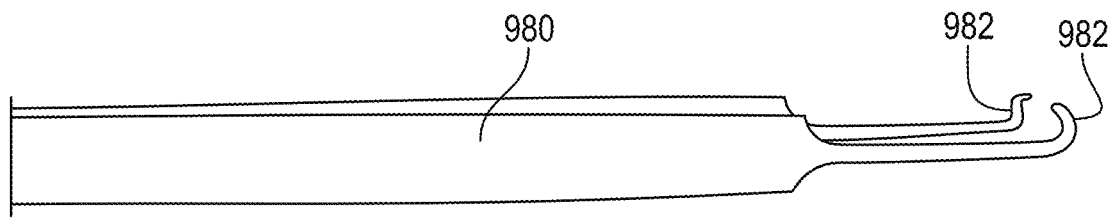
FIGS. 9A-9D is the schematic diagram of a specific embodiment of folding device.
Figure 9B:
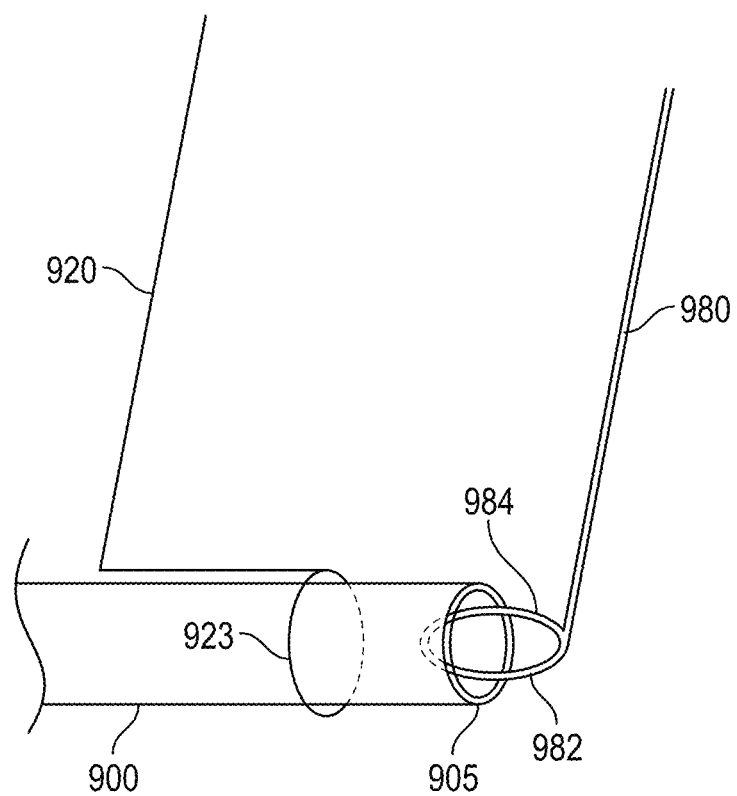
Figure 9C:
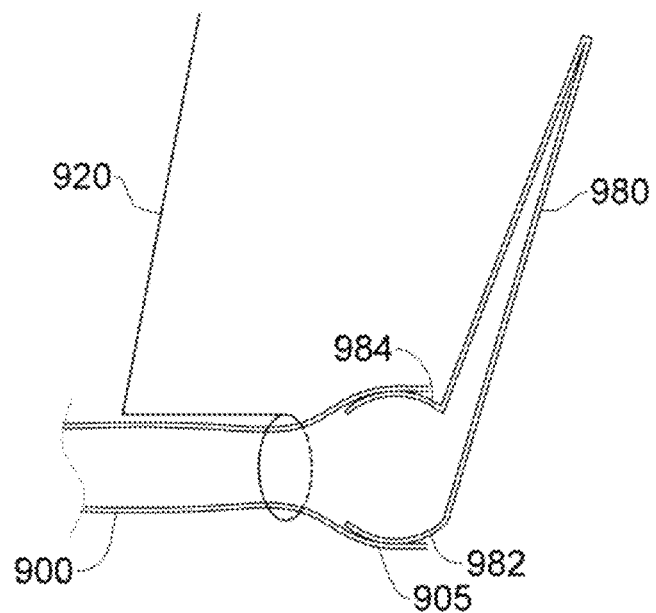
Figure 9D:
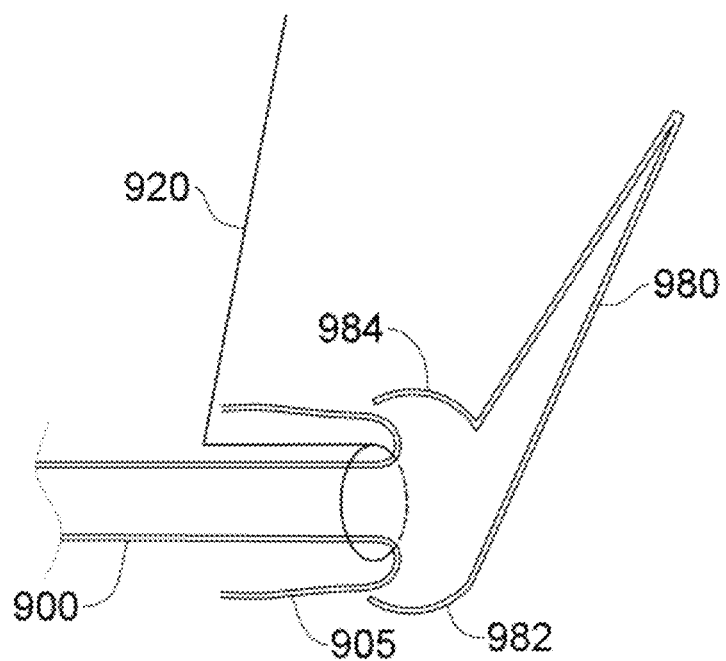

Referring now to FIGS. 9A-9D, FIG. 9A is the schematic diagram of a specific embodiment of folding device, and FIGS. 9B-9D describe a specific embodiment of using the folding device to fold the end of target to be anastomosed to the telescoping part of manipulator. As shown in the embodiment of FIG. 9A, the folding device 980 includes the first folding part 982 and the second folding part 984. As shown in the embodiment of FIG. 9B, after telescoping the telescoping part 923 of the manipulator 920 to the end to be anastomosed 905 of the target to be anastomosed 900, mutually close the first folding part 982 and second folding part 984 of the folding device 980 first, and then embed them into the end to be anastomosed 905 of the target to be anastomosed 900. Then, as shown in FIG. 9C, after embedding the first folding part 982 and second folding part 984 into the end to be anastomosed 905, mutually open the first folding part 982 and second folding part 984 to distract the end to be anastomosed 905. After that, as shown in FIG. 9D, push the first folding part 982 and second folding part 984 towards the telescoping part 923, so as to fold the distracted end to be anastomosed 905 to the telescoping part 923. And the folding operation will be finished in this way.

Referring to FIGS. 10A-10G, anastomosis set 1000 includes a manipulator 1020, an anastomosis mechanism 1050, an anastomotic auxiliary 1050, and a makeup mechanism 1060. The manipulator 1020 includes a telescoping part 1023, and the anastomotic auxiliary 1050 has an exit part 1052 and a convex part 1054. In some examples, the anastomotic auxiliary 1050 is flexible.

Referring to FIGS. 10A-10G, the telescoping part 1023 is used for telescoping to the end to be anastomosed 905 of the target to be anastomosed 900. The manipulator 1020 has an exit part, after the target to be anastomosed 900 has been anastomosed, the manipulator 1020 can be removed from the target to be anastomosed 900 through the exit part. According to one example, the manipulator exit part is the gap at the telescoping part 1023. Please note that in some examples, the structure of manipulator 1023 may be as shown from FIG. 2A to FIG. 2D.

Figure 10A:
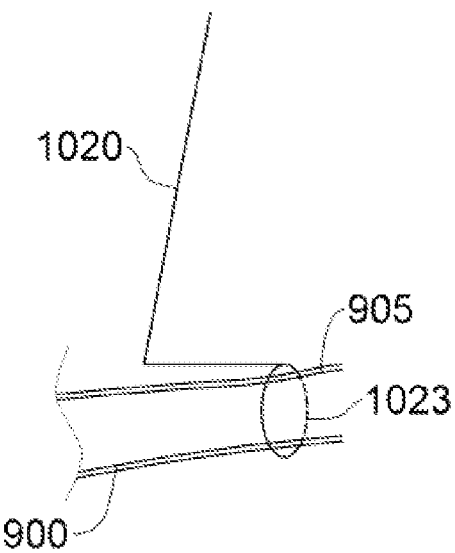
FIGS. 10A-10G is the application schematic diagram of a specific embodiment of anastomosis set in this Invention.
Figure 10B:
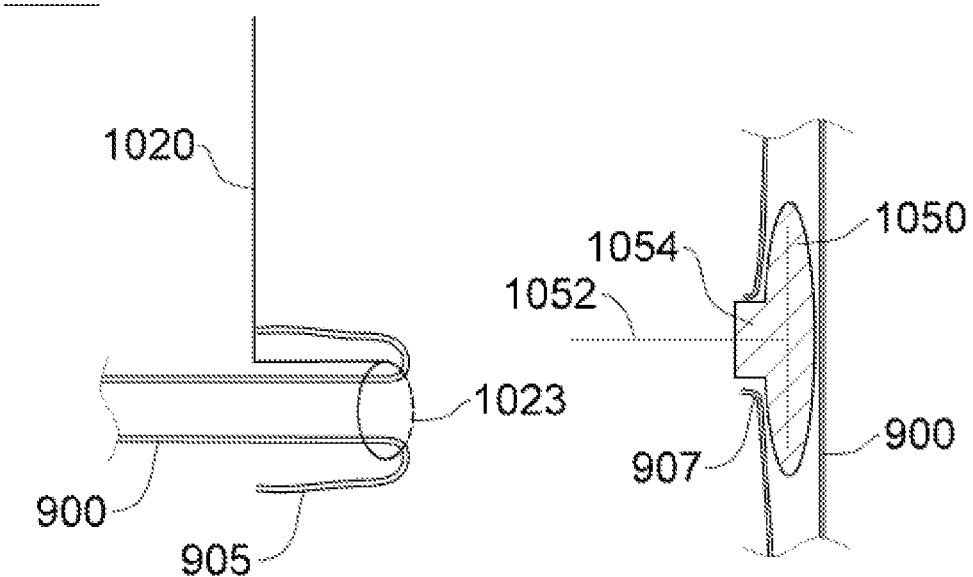

Turning to FIG. 10A, when using the anastomosis set 1000, telescope the telescoping part 1023 of the manipulator 1020 to the end to be anastomosed 905 of the target to be anastomosed 900 first. Then, as shown in FIG. 10B, fold the end to be anastomosed 905 of the target to be anastomosed 900 at the telescoping part 1023 of the manipulator 1020, and embed the anastomotic auxiliary 1050 from the side to be anastomosed 907 of the target to be anastomosed 900. Meanwhile, fold the side to be anastomosed 907 outward through the convex part 1054 of the anastomotic auxiliary 1050. When folding the end to be anastomosed 905 at the telescoping part 1023, the processes as shown from FIG. 9A to 9D may be used, but the invention is not limited to this.

Figure 10C:
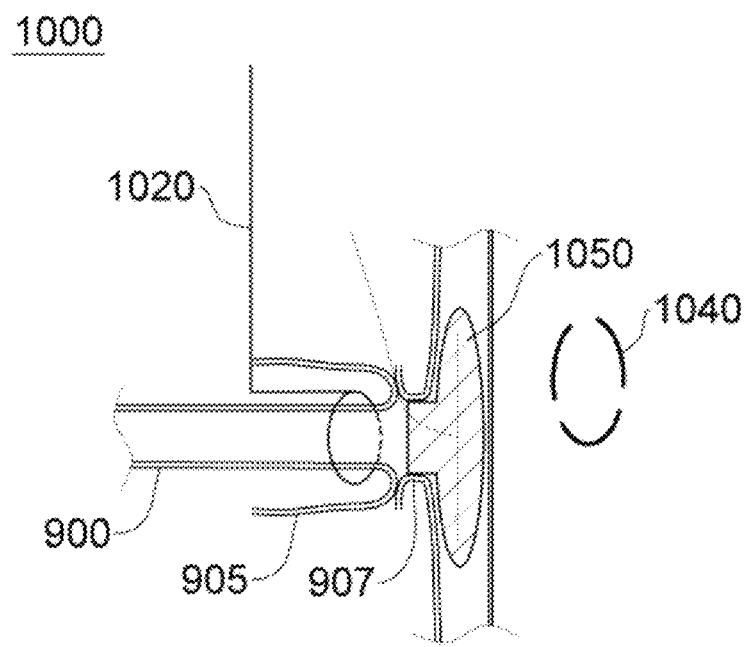
Figure 10D:
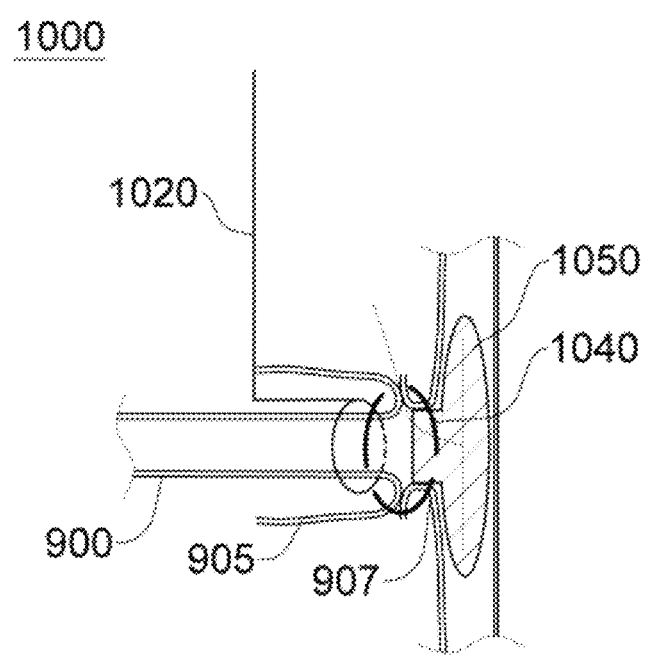
Figure 10E:
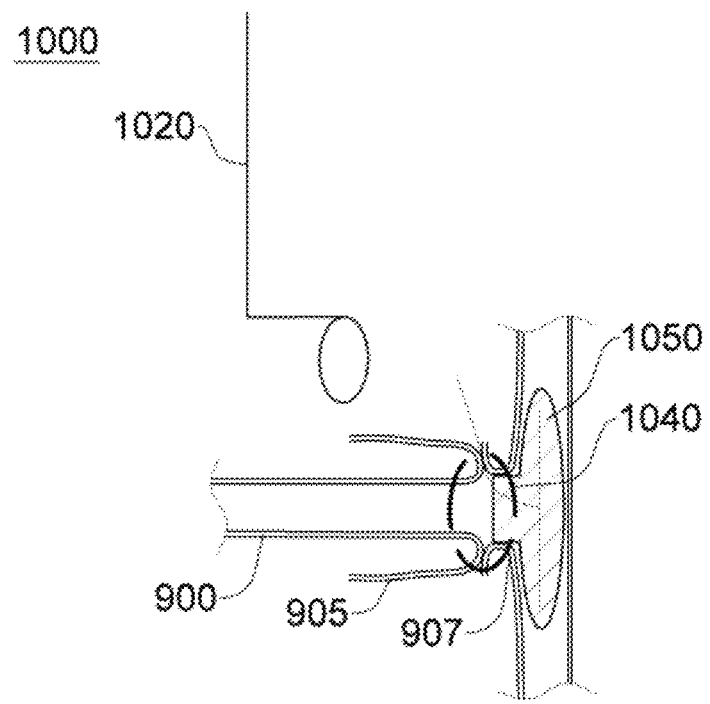

Referring now to FIG. 10C, fold the end to be anastomosed 905 outward using the telescoping part 1023 such that it mutually aligns with the side to be anastomosed 907. After that, as shown in FIG. 10D, use the anastomosis mechanism 1040 to anastomose the end to be anastomosed 905 with the side to be anastomosed 907 folding outward. The anastomosis mechanism 1040 and the method thereof may be referred to as shown from FIG. 3A to FIG. 3E, but the invention is not limited to this. It should be noted that, when using the anastomosis mechanism 1040 to anastomose the end to be anastomosed 905 with the side to be anastomosed 907, a certain gap between the end to be anastomosed 905 and the side to be anastomosed 907 needs to be reserved, thus total or complete anastomosis is not necessary.

Figure 10F:
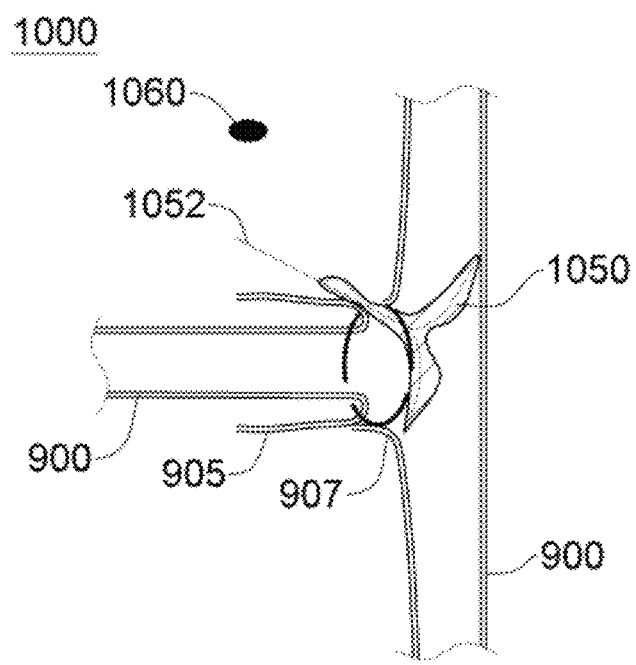
Figure 10G:
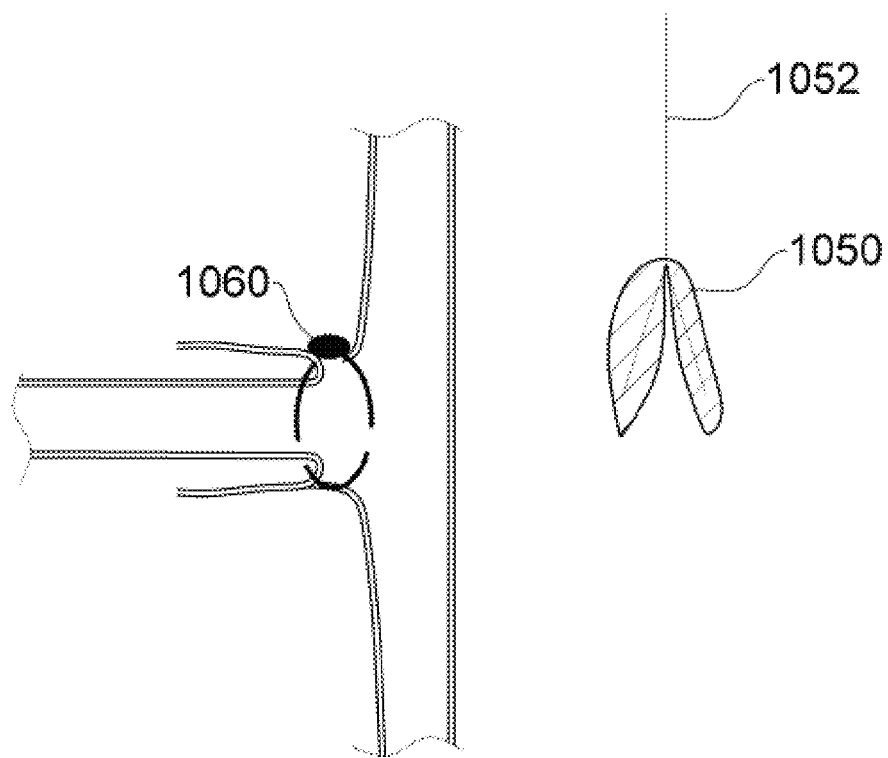

Referring to 10E, after using the anastomosis mechanism 1040 to anastomose the end to be anastomosed 905 with the side to be anastomosed 907, remove the manipulator 1020 from the target to be anastomosed 900 through the exit part. After that, as shown in FIG. 10F, remove the anastomotic auxiliary 1050 outward from the un-anastomosed gap by pulling the anastomotic auxiliary exit part 1052. Finally, as shown in FIG. 10G, use makeup mechanism 1060 to make up (close) the aforementioned un-anastomosed gap. In some examples, the makeup mechanism may be, but not limited to, suture mechanism, bonding mechanism, buckling mechanism, clamping mechanism and nailing mechanism etc.

Figure 11A:
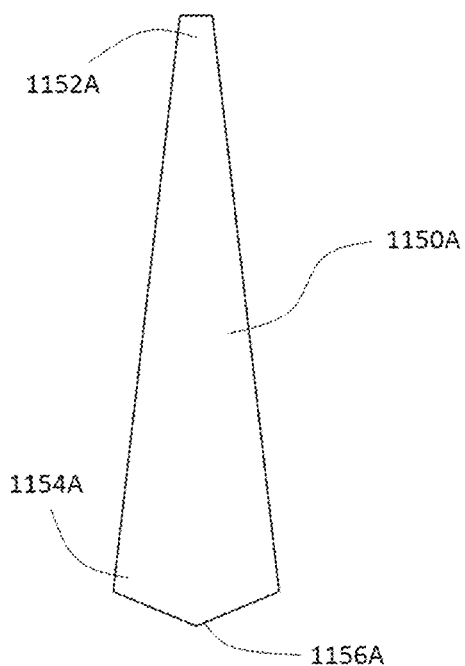
FIGS. 11A-11D is the schematic diagram of a specific embodiment of long flake.
Figure 11B:
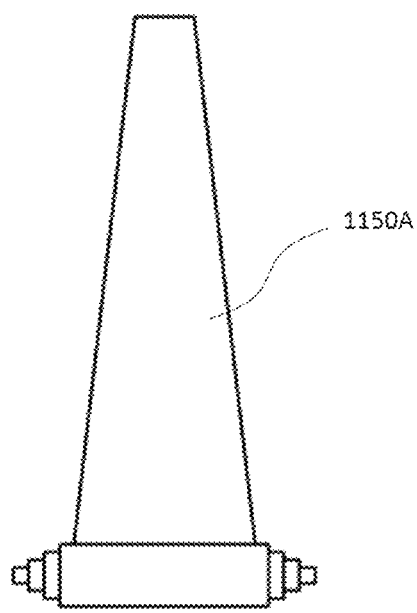
Figure 11C:
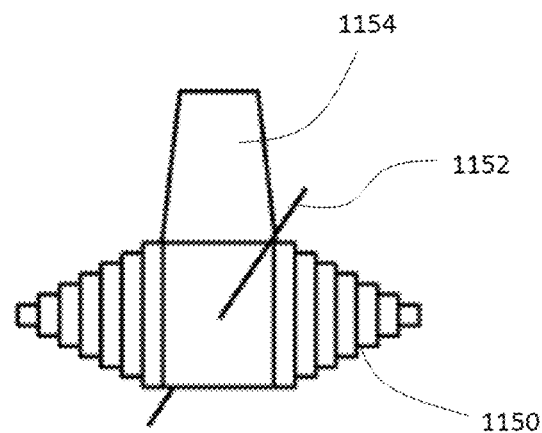

Referring to FIG. 11A to FIG. 11C, examples thereof describe the anastomotic auxiliary of a specific embodiment and the making method thereof. As shown in the examples illustrated in FIGS. 11A-11C, the anastomotic auxiliary 1150 is formed by winding an elongate ribbon, strip of sheet 1150A. Among them, the elongate ribbon 1150A has the upper part 1152A and lower part 1154A. The width of the ribbon 1150A increases gradually from the upper part 1152A to the lower part 1154A. In different specific embodiments, the ribbon 1150A may have different thicknesses in different parts to obtain the anastomotic auxiliary 1150 of different curvatures. For example, the thickness of the elongate ribbon 1150A may decrease gradually from the upper part 1152A to the lower part 1154A, so as to make the anastomotic auxiliary 1150 have a greater curvature. As shown in the example of FIG. 11A, the elongate ribbon 1150A also has the tip end 1156A, thus user may easily wind the ribbon 1150A from the tip end 1156A.

As shown in the embodiment of FIG. 11C, the anastomotic auxiliary 1150 has the fusiform fixing mechanism 1152 and the unwound recycle unit 1154. In a specific embodiment, when removing the anastomotic auxiliary 1150 outward from the un-anastomosed gap of the target to be anastomosed, release the fusiform fixing mechanism 1152 first, and then remove the anastomotic auxiliary 1150 outward from the un-anastomosed gap by pulling the recycle unit 1154. In the process of pulling, the anastomotic auxiliary 1150 will be unfolded from the wound status gradually and restore into the elongate ribbon 1150A as shown in FIG. 11A. Please note that, the fusiform fixing mechanism 1152 is only an example here, the fusiform fixing mechanism of anastomotic auxiliary may be a buckling mechanism, clamping mechanism, nailing mechanism or bonding mechanism as needed, or the ribbon itself may have viscosity or frictional force, or any wound ribbon may be fixed temporarily as the fixing mechanism of the anastomotic auxiliary.

Figure 11D:
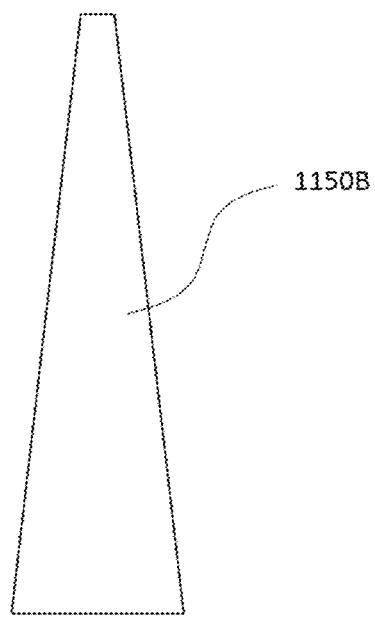

Please note that, the elongate ribbon 1150A in FIG. 11A is only an example here, it may have different shapes in different embodiments. FIG. 11D describes the elongate ribbon 1150B of different tip ends.

Figure 12A:
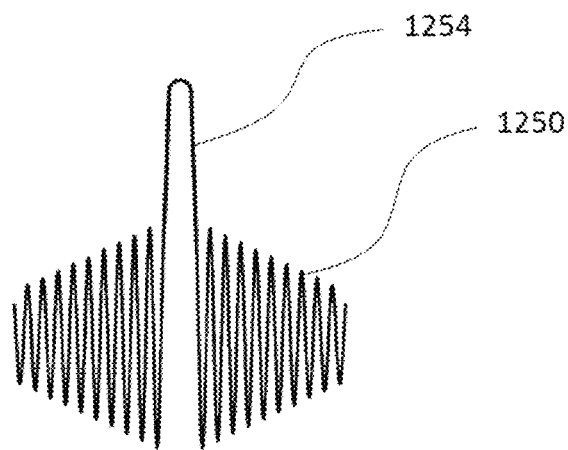
FIGS. 12A-12C is the schematic diagram of a specific embodiment of anastomotic auxiliary.
Figure 12B:
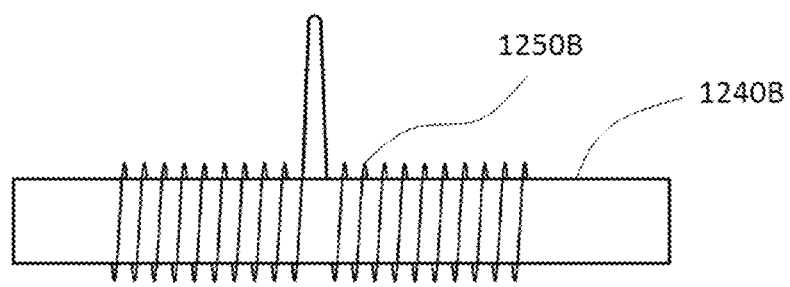
Figure 12C:
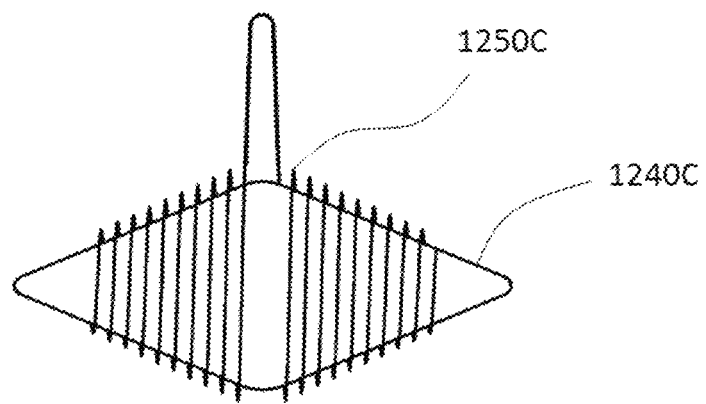

Referring to FIGS. 12A-12C, anastomotic auxiliary 1250 may be formed by at least one line. Among them, the anastomotic auxiliary 1250 has the recycle unit 1254. When removing the anastomotic auxiliary 1250 from the un-anastomosed gap of the target to be anastomosed, the anastomotic auxiliary 1250 may be removed by pulling the recycle unit 1254. In the process of pulling, the anastomotic auxiliary 1250 will be unfolded from the wound status gradually and restored onto the line. According to one example, the anastomotic auxiliary 1250 is formed from a shape-memory metal such as a nickel-titanium alloy, the anastomotic auxiliary 1250 will restore from the line into anastomotic auxiliary by itself after being removed from the un-anastomosed gap of the target to be anastomosed. FIG. 12B describes an example of winding the line 1250B spirally with the assistive device 1240B. In this example, after winding the line 1250B spirally with the assistive device 1240B, the wound line 1250B may be further adjusted to form the anastomotic auxiliary. FIG. 12C describes an example of winding the line 1250C into the anastomotic auxiliary with the assistive device 1240C.

According to one example, the materials of anastomotic auxiliary as shown in FIGS. 11A-11D may be, but not limited to, plastic, paper, metal, memory metal, titanium, stainless steel, aluminum, rubber, cloth, silica gel or plastic material. In other examples, the materials of anastomotic auxiliary as shown in FIGS. 11A-11C may be, but not limited to, metal, memory metal, titanium, stainless steel or aluminum.

Figure 13:
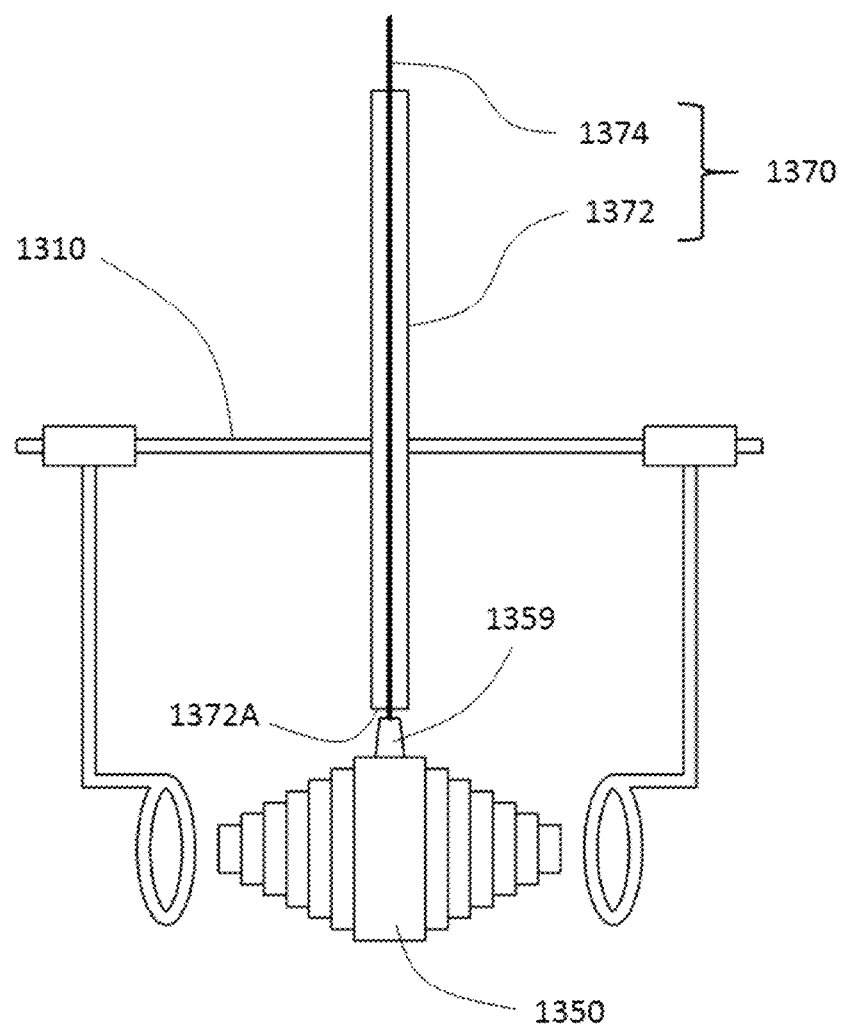
FIG. 13 is the schematic diagram of a specific embodiment of anastomotic auxiliary and anastomotic auxiliary removal aid.

Referring to FIG. 13A, the anastomotic auxiliary 1350 is formed by winding an elongate ribbon 1150A, and the anastomotic auxiliary 1350 has the recycle unit 1359. The recycle unit 1359 is connected to one end of the removal device 1374 of anastomotic auxiliary removal aid 1370. The anastomotic auxiliary removal aid 1370 includes a hollow tube 1372 and removal device 1374, and the removal device 1374 is situated in the access of hollow tube 1372. Pulling one end of the removal device 1374, will withdraw the anastomotic auxiliary 1350 along the access of hollow tube 1372. According to one example, the tube diameter of the front end 1372A of hollow tube 1372 is smaller, when the anastomotic auxiliary 1350 is entering into the access of hollow tube 1372, the anastomotic auxiliary 1350 is unwound because it is squeezed by the front end 1372A, and restores into the elongate ribbon gradually. In a specific embodiment, the anastomotic auxiliary removal aid 1370 is connected to the anastomotic aid device 1310. In another specific embodiment, the anastomotic auxiliary removal aid 1370 and anastomotic aid device 1310 are separate.

Figure 14:
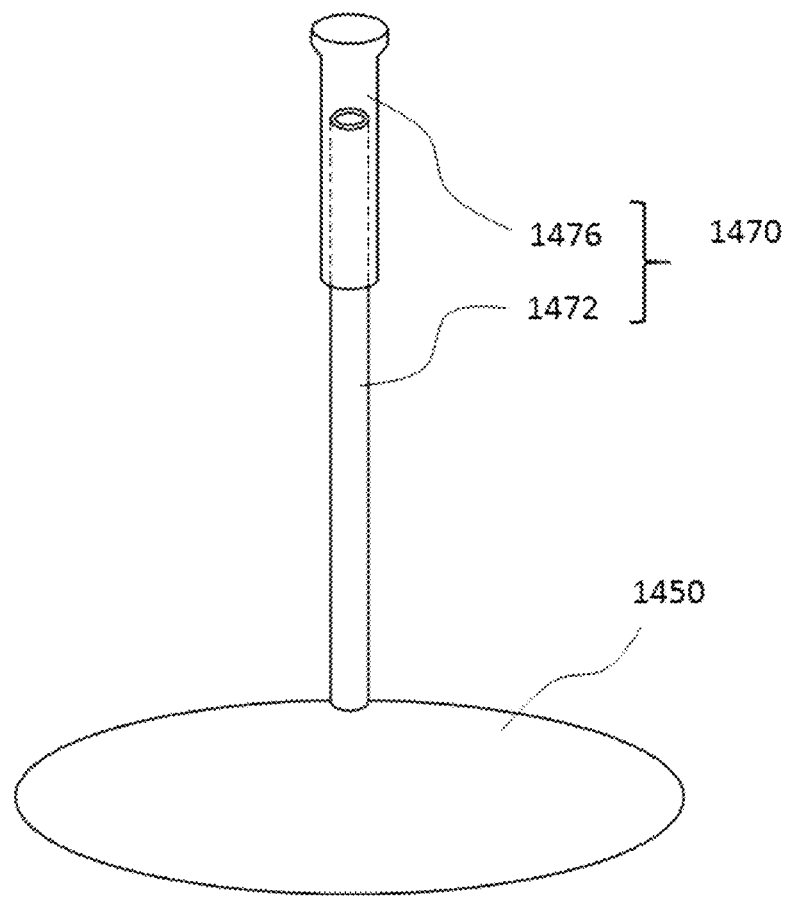
FIG. 14 is the schematic diagram of a specific embodiment of anastomotic auxiliary and anastomotic auxiliary removal aid.

Referring to FIG. 14, the anastomotic auxiliary 1450 is a balloon, in which gas and/or liquid may be filled. Among them, the anastomotic auxiliary 1450 has a valve or an opening-closing hole, to which the hollow tube 1472 of the anastomotic auxiliary removal aid 1470 is connected. Thus, through the filling part 1476 of anastomotic auxiliary removal aid 1470, the anastomotic auxiliary removal aid 1470 may fill the gas and/or liquid to the anastomotic auxiliary 1450, or extract the gas and/or liquid from the anastomotic auxiliary 1450. In some examples, the filling part 1476 may be a syringe, or other devices may assist in filling or extracting gas and/or liquid. In one example, the anastomotic auxiliary removal aid 1470 may further include a removal device in the access of hollow tube 1472.

Figure 15:
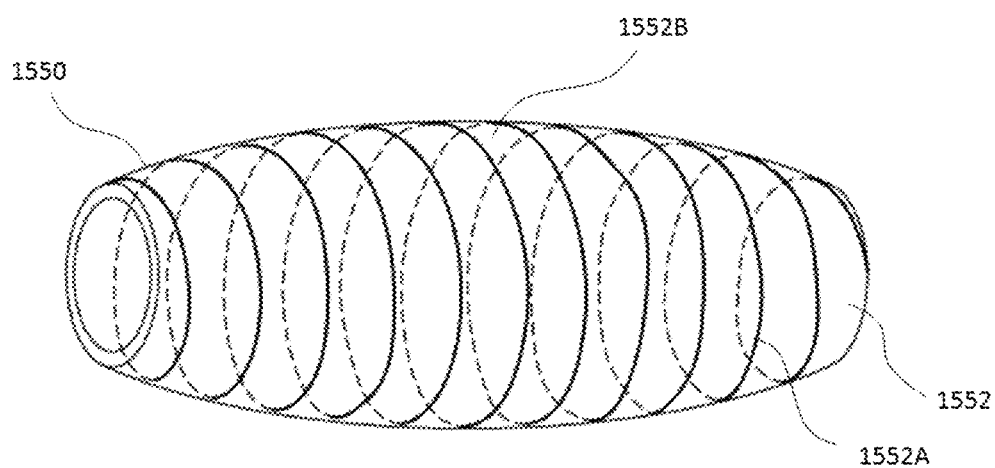
FIG. 15 is the schematic diagram of a specific embodiment of anastomotic auxiliary.

Referring to FIG. 15, anastomotic auxiliary 1550 includes the fusiform body 1552, and the fusiform body 1552 has the recycle unit 1552B and a tear line 1552A extending spirally on the fusiform body 1552. Pulling the recycle unit 1552A causes the fusiform body 1552 to be torn gradually along the tear line 1552A, and turn into a linear body gradually. According to one example, the recycle unit of fusiform body 1552 is set close to the opening of fusiform body 1552. According to one example, the fusiform body 1552 is not completely separated at the tear line 1552A, hence it may maintain a tubular shape before pulling the recycle unit 1552A. According to one example, the fusiform body 1552 is completely separated at the tear line 1552A, through a bonding mechanism, it maintains a tubular shape before pulling the recycle unit 1552A. According to one example, the component 1550 may be of tubular structure as needed.

Figure 16:
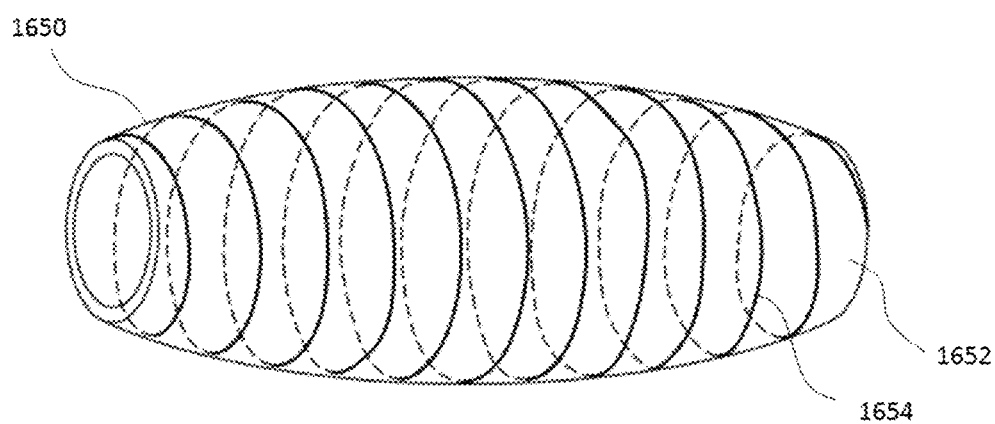
FIG. 16 is the schematic diagram of a specific embodiment of anastomotic auxiliary.

Referring to FIG. 16, anastomotic auxiliary 1650 includes the fusiform body 1652 and the metal line 1654 wound on the fusiform body. The metal line 1654 may support the fusiform body 1652. Please note that, FIG. 16 is an example only, the metal line 1654 may not only be wound spirally on the fusiform body 1652, it may be placed at the fusiform body 1652 in different forms as needed. THE component 1650 may be of tubular structure as needed.

Figure 17A:
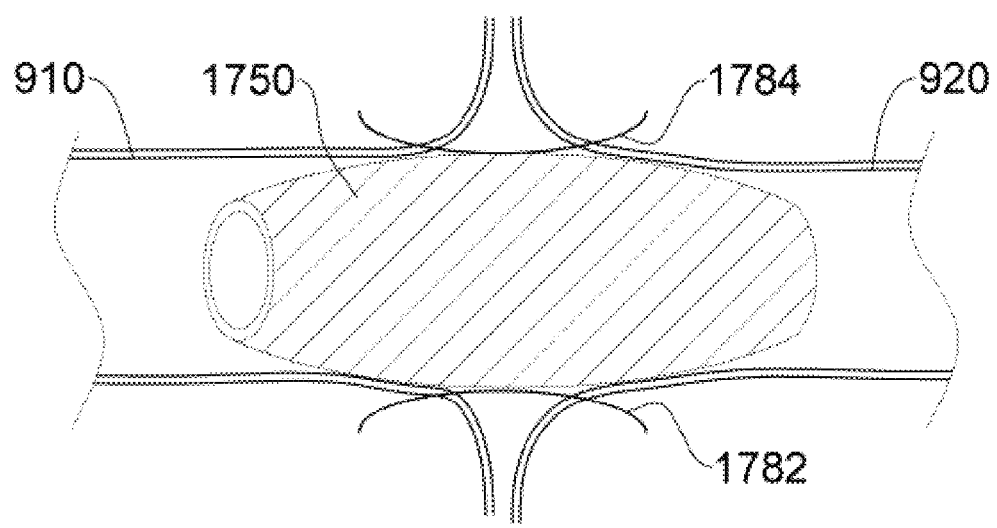
FIGS. 17A-17B is the schematic diagram of a specific embodiment of anastomotic auxiliary and anastomosis mechanism.
Figure 17B:
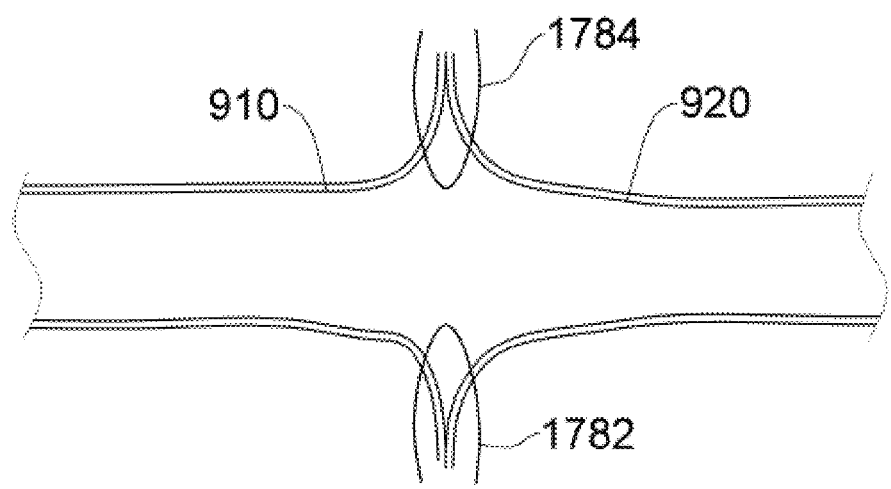

FIGS. 17A and 17B describe an anastomosis mechanism includes the C-shape devices 1782 and 1784. The anastomotic auxiliary 1750 is the solid substance dissoluble in human body, among them, when such solid substance is dissolving, the C-shape devices 1782 and 1784 will anastomose the first end to be anastomosed 910 with the second end to be anastomosed 920.

One of ordinary skill in the art will appreciate that all of the exemplary anastomotic auxiliaries mentioned above are examples only. The anastomotic auxiliary may have different types of execution, for example, lines may be stacked into the solid tubular shape or solid fusiform shape to be used as the anastomotic auxiliary, or the fusiform solid substance that can be dissolved or degraded in human body (such as ice cube, or ice cube of normal saline) may be used as the anastomotic auxiliary, but not limited to this. Besides, in different embodiments, when the first embedding end of anastomotic auxiliary is embedded into the first end to be anastomosed, and the second embedding end is embedded into the second end to be anastomosed, the anastomotic auxiliary may turn into, but not limited to, any one of fusiform, tubular, rectangular, oval, flying saucer or cylindrical shape.

According to one example, the anastomosis set may not include the first manipulator, the second manipulator and the anastomotic aid device. The anastomosis set in this specific embodiment includes anastomotic auxiliary, anastomotic device and makeup mechanism. Among them, user embeds the first embedding end of anastomotic auxiliary into the first end of the target to be anastomosed first, and embeds the second embedding end of anastomotic auxiliary into the second end of the target to be anastomosed first. Then make the first end and second end mutually align to each other, after doing so, let the body fluids flow in a hollow tube of the anastomotic auxiliary. After that, use the anastomosis mechanism to anastomose the first end with the second end. In a specific embodiment, the anastomotic auxiliary used is the anastomotic auxiliary that will not be dissolved in body fluids. Therefore, it is further needed to remove the anastomotic auxiliary from the target to be anastomosed, and use a makeup mechanism to make up the un-anastomosed gap of the target to be anastomosed after that.

According to one example, the materials of anastomotic auxiliary may be, but not limited to, any one of the following: plastic, paper, metal, magnesium alloy, memory metal, titanium, stainless steel, aluminum, rubber, cloth, silica gel or plastic material, ice cube of normal saline, ice cube, carbohydrate, PLA (Poly Lactic Acid), PGA (Poly Glutamic Acid), or ceramic. In different specific embodiments, any other materials of medical use may be used as the materials of anastomotic auxiliary as needed.

Figure 18A:
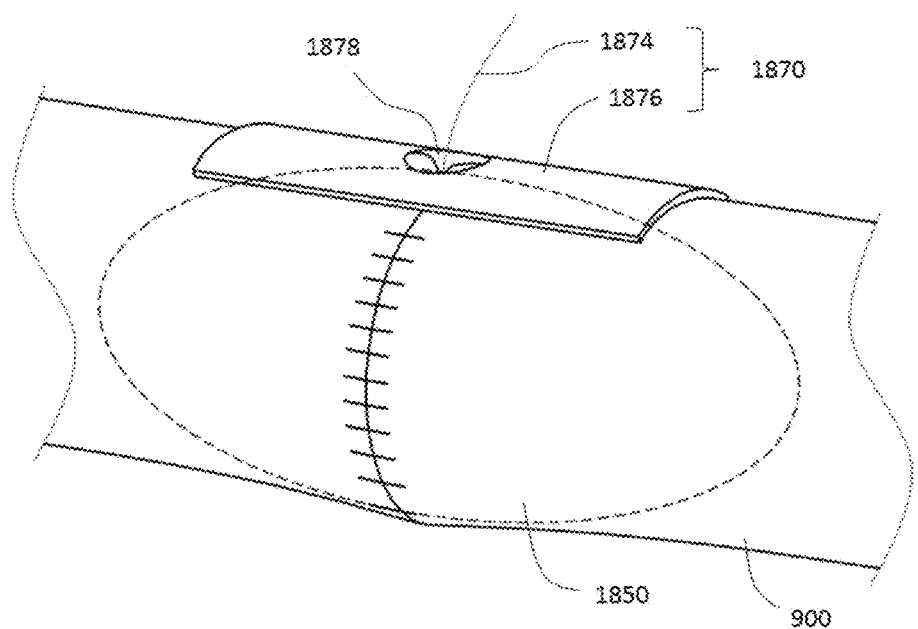
FIGS. 18A-18B is the schematic diagram of a specific embodiment of anastomotic auxiliary removal aid.
Figure 18B:
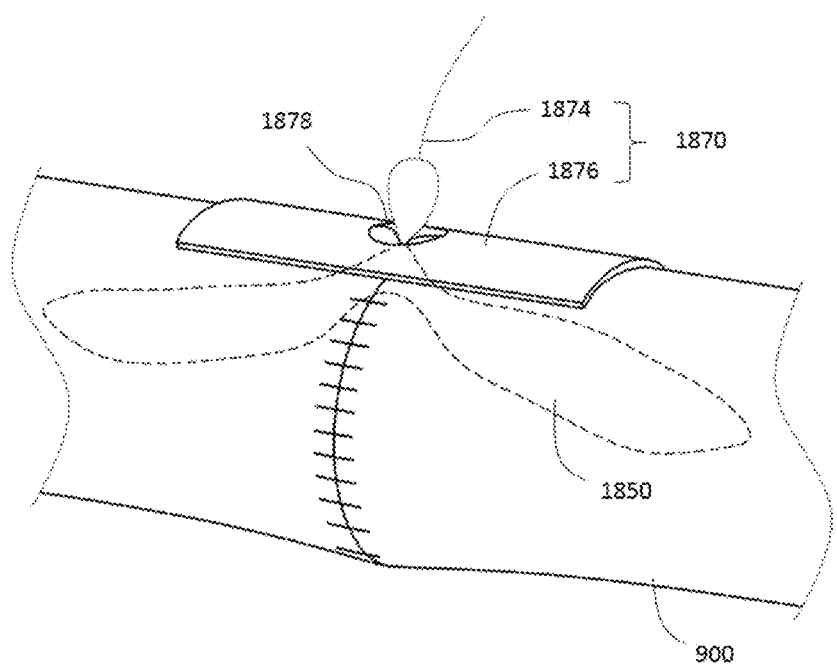

FIGS. 18A and 18B describe an anastomotic auxiliary removal aid 1870 including removal device 1874 and arcuate sheet component 1876. Removal hole 1878 is defined in arcuate sheet component 1876, and the removal device 1874 connects to the anastomotic auxiliary 1850 through the removal hole 1878. In this way, by pulling the removal device 1874, a user can remove the anastomotic auxiliary 1850 from the un-anastomosed gap of the target to be anastomosed 900 through removal hole 1878, and then make up the un-anastomosed gap after removing the anastomotic auxiliary 1850. In a specific embodiment, the removal hole 1878 is slightly smaller than the pore diameter of un-anastomosed gap, thus it can avoid enlarging the pore diameter of un-anastomosed gap in the course of removing the anastomotic auxiliary 1850. In different specific embodiments, the removal hole 1878 substantially equals to the pore diameter of the un-anastomosed gap, or is only slightly larger than the pore diameter of the un-anastomosed gap.

In a specific example, the anastomosis set means the set used for anastomosis surgery. Please be aware that, the anastomosis set in the present invention may also be applied to various anastomosis surgeries, for example, it may be applied to the anastomosis of large and small intestine, ureter or bile duct etc.

The anastomosis of the present invention has been described through the above descriptions and drawings. However, the specific examples disclosed herein are used for description only, and they may be changed without departing from the scope and spirit of claims, and they shall all be included in the patent scope of this invention. Therefore, all specific examples described in this description are not used for restricting this invention.

The invention claimed is:

1. An anastomosis set for anastomosing a first end to be anastomosed with a second end to be anastomosed, the anastomosis set comprising:
    a first manipulator, with a first telescoping part at a distal end of the first manipulator, the first telescoping part is used for telescoping toward the first end to be anastomosed;
    a second manipulator, with a second telescoping part at a distal end of the second manipulator, the second telescoping part is used for telescoping toward the second end to be anastomosed;
    an anastomosis mechanism for anastomosing the first end to be anastomosed with the second end to be anastomosed;
    an anastomotic auxiliary having a first embedding end and a second embedding end; wherein the first embedding end is configured to embed into a first end of a blood vessel to be anastomosed, and the second embedding end is configured to embed into a second end of the blood vessel to be anastomosed;
    the first manipulator including a first exit part through which the first manipulator will be removed from the first end to be anastomosed after anastomosing;
    the second manipulator has a second exit part, through which the second manipulator will be removed from the second end to be anastomosed after anastomosing; and
    wherein the anastomotic auxiliary is configured to be removed from the first end to be anastomosed and the second end to be anastomosed after the first end to be anastomosed is anastomosed with the second end to be anastomosed;

wherein the anastomotic auxiliary has a recycle unit, and a tear line is formed by extending spirally on the anastomotic auxiliary; wherein when pulling the recycle unit, the anastomotic auxiliary is gradually torn into a linear body along the tear line.

2. The anastomosis set of claim 1, wherein a metal line is wound onto the anastomotic auxiliary to support it.

3. The anastomosis set of claim 1, wherein the anastomotic auxiliary has a hollow tube for body fluids to flow in it.

4. An anastomosis set, comprising:
an anastomotic auxiliary, at least a part of it is embedded into a body part to be anastomosed; and
an anastomotic device, which anastomoses the body part to be anastomosed after the anastomotic auxiliary is embedded into the body part to be anastomosed;
wherein the anastomotic auxiliary is embedded into the body part to be anastomosed in a first structural form and removed from the body part to be anastomosed in a second structural form, and the first structural form is different from the second structural form;
wherein the anastomotic auxiliary has a first embedding end and a second embedding end;
wherein the first embedding end is configured to embed into a first end of a blood vessel to be anastomosed, and the second embedding end is configured to embed into a second end of the blood vessel to be anastomosed;
wherein the anastomotic auxiliary has a recycle unit, and a tear line is formed by extending spirally on the anastomotic auxiliary;
wherein when pulling the recycle unit, the anastomotic auxiliary is gradually torn into a linear body along the tear line.

5. The anastomosis set of claim 4, wherein the anastomotic auxiliary includes a recycle unit, and a tear line is formed by extending spirally on the anastomotic auxiliary; wherein when pulling the recycle unit, the anastomotic auxiliary is gradually torn into a linear body along the tear line.

6. The anastomosis set of claim 4, wherein a metal line is wound onto the anastomotic auxiliary to support it.

7. The anastomosis set of claim 4, further comprising an anastomotic auxiliary removal aid, the anastomotic auxiliary removal aid removes the anastomotic auxiliary from the body part to be anastomosed; wherein the anastomotic auxiliary removal aid includes a hollow tube and a removal device; wherein the hollow tube has an access in which the removal device locates; wherein the removal device connects the anastomotic auxiliary.

* * * * *